(12) United States Patent
Bilsborough

(10) Patent No.: US 10,611,846 B2
(45) Date of Patent: *Apr. 7, 2020

(54) METHODS OF TREATING SKIN DISORDERS USING ANTI-IL-31RA ANTIBODIES

(71) Applicant: ZymoGenetics, Inc., Princeton, NJ (US)

(72) Inventor: Janine M. Bilsborough, Simi Valley, CA (US)

(73) Assignee: ZymoGenetics, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,070

(22) Filed: Apr. 23, 2018

(65) Prior Publication Data

US 2018/0244790 A1    Aug. 30, 2018

Related U.S. Application Data

(60) Continuation of application No. 15/839,362, filed on Dec. 12, 2017, now abandoned, which is a continuation of application No. 15/615,567, filed on Jun. 6, 2017, now abandoned, which is a continuation of application No. 15/411,640, filed on Jan. 20, 2017, now abandoned, which is a continuation of application No. 14/829,711, filed on Aug. 19, 2015, now abandoned, which is a division of application No. 12/986,707, filed on Jan. 7, 2011, now Pat. No. 9,139,651, which is a division of application No. 12/404,162, filed on Mar. 13, 2009, now Pat. No. 7,871,618, which is a continuation of application No. 11/353,451, filed on Feb. 14, 2006, now abandoned.

(60) Provisional application No. 60/716,761, filed on Sep. 13, 2005, provisional application No. 60/694,867, filed on Jun. 29, 2005, provisional application No. 60/653,283, filed on Feb. 14, 2005.

(51) Int. Cl.
| | |
|---|---|
| *A61K 39/395* | (2006.01) |
| *C07K 16/28* | (2006.01) |
| *C07K 14/715* | (2006.01) |
| *A61K 39/00* | (2006.01) |

(52) U.S. Cl.
CPC ...... *C07K 16/2866* (2013.01); *C07K 14/7155* (2013.01); *A61K 39/00* (2013.01); *A61K 2039/505* (2013.01); *C07K 2317/24* (2013.01); *C07K 2317/76* (2013.01)

(58) Field of Classification Search
CPC .......................................... A61K 2039/55527
See application file for complete search history.

(56) References Cited

U.S. PATENT DOCUMENTS

| | | | |
|---|---|---|---|
| 7,064,186 B2 | 6/2006 | Sprecher et al. | |
| 7,494,804 B2 | 2/2009 | Sprecher et al. | |
| 7,514,077 B2 | 4/2009 | Yao et al. | |
| 7,638,126 B2 | 12/2009 | Yao et al. | |
| 7,871,618 B2 * | 1/2011 | Bilsborough ...... | C07K 16/2866 |
| | | | 424/139.1 |
| 7,939,068 B2 | 5/2011 | Yao et al. | |
| 7,943,132 B2 | 5/2011 | Yao et al. | |
| 8,017,122 B2 | 9/2011 | Siadak et al. | |
| 8,105,590 B2 | 1/2012 | Yao et al. | |
| 8,105,591 B2 | 1/2012 | Yao et al. | |
| 8,377,438 B2 | 2/2013 | Yao et al. | |
| 8,409,571 B2 | 2/2013 | Yao et al. | |
| 8,388,964 B2 | 3/2013 | Leung et al. | |
| 8,466,262 B2 | 6/2013 | Siadak et al. | |
| 8,568,723 B2 | 10/2013 | Siadak et al. | |
| 8,637,015 B2 | 1/2014 | Yao et al. | |
| 8,685,395 B2 | 4/2014 | Yao et al. | |
| 8,778,344 B2 | 7/2014 | Sprecher et al. | |
| 8,968,732 B2 | 3/2015 | Yao et al. | |
| 8,974,783 B2 | 3/2015 | Yao et al. | |
| 9,011,858 B2 | 4/2015 | Siadak et al. | |
| 9,334,321 B2 | 5/2016 | Yao et al. | |
| 9,334,322 B2 | 5/2016 | Yao et al. | |
| 2004/0142422 A1 | 7/2004 | Sprecher et al. | |
| 2004/0152161 A1 | 8/2004 | Cosman et al. | |
| 2013/0177563 A1 | 7/2013 | Leung et al. | |
| 2015/0344581 A1 | 12/2015 | Bilsborough et al. | |
| 2017/0137525 A1 | 5/2017 | Bilsborough et al. | |
| 2017/0275369 A1 | 9/2017 | Bilsborough et al. | |

FOREIGN PATENT DOCUMENTS

| | | |
|---|---|---|
| WO | 00/75314 A1 | 12/2000 |
| WO | 02/00690 A2 | 1/2002 |
| WO | 02/00721 A2 | 1/2002 |
| WO | 02/29060 A2 | 4/2002 |
| WO | 02/77230 A1 | 10/2002 |

(Continued)

OTHER PUBLICATIONS

Aioi, A. et al., *Br J. Dermatol* 144(1):12-18, 2001.
Akdis, C.A., et al., *J. Invest. Dermatol.* 113(4) 628-34, 1999.
Aleksza, M., et al., *Br. J. Dermatol.* 147(6):1135-41, 2002.
Antunez, C., et al., *Clin. Exp. Allergy* 34(4) 559-66, 2004.
Asadullah, K. et al., *Arch. Dermatol* 138(9):1189-96, 2002.
Askenase, P.W., *Chem. Immunol.* 78:112-23, 2000.
Barnes, K.C., et al., *Genomics* 37(1):41-50, 1996.
Berger, C.L., et al., *Blood* 105(4):1640-7, 2005.

(Continued)

*Primary Examiner* — Prema M Mertz
(74) *Attorney, Agent, or Firm* — Brian J. Walsh

(57) ABSTRACT

The present invention relates to methods of treating patients suffering from Contact dermatitis, Drug induced delayed type cutaneous allergic reactions, Toxic epidermal necrolysis, Cutaneous T cell Lymphoma, Bullous pemphigoid, Alopecia aereata, Vitiligo, Acne Rosacea, Prurigo nodularis, Scleroderma, Herpes simplex virus, or combination by administering an IL-31RA antagonist.

5 Claims, No Drawings

Specification includes a Sequence Listing.

(56) References Cited

FOREIGN PATENT DOCUMENTS

| WO | 03/060090 A2 | 7/2003 |
| WO | 03/072740 A2 | 9/2003 |
| WO | 04/003140 A2 | 1/2004 |

OTHER PUBLICATIONS

Bilsborough, J. et al., *J. Allergy Clin. Immunol. 117(2)*:418-25, 2006.
Bonecchi, R., et al., *J. Exp. Med. 187(1)*:129-34, 1998.
Dillon S.R., et al., *Nat. Immunol. 5(7)*:752-60, 2004.
Dillon, S.R., et al., *Nat. Immunol. 6(1)*:114, 2005.
Diveu, C., et al., *Eur. Cytokine Netw. 15(4)*:291-302, 2004.
Diveu, C., et al., *J. Biol. Chem. 278(50)*:49850, 2003.
Dreuw, A., et al., *Immunobiology 210(6-8)*, 454, 2005.
Dreuw, A., et al., Keystone Symposia "Cytokines, Disease and Therapeutic Intervention," Feb. 12-17, 2005.
Dreuw, A., et al., *J. Biol. Chem. 279(34)*:36112-20, 2004.
Fang, D., et al., *Nat. Immunol. 3(3)*:281-7, 2002.
Ghilardi, N. et al., *J. Biol. Chem. 277(19)*:16831, 2002.
Gutermuth, J. et al., *Int. Arch. Allergy Immunol. 135(3)*:262-76, 2004.
Hammond, A., et al., Orphan class I cytokine receptor Zcytor17 is upregulated in activated monocytes and T cells. (W-2-4) S48.
Hashimoto, Y., et al., *Life Sci. 76(7)*:783-94, 2004.
Hashimoto, Y., et al., *J. Dermatol. Sci. 35(2)*:143-50, 2004.
Hermanns, H.M., et al., *Experimental Dermatology 15(N3)*:219-20, 2006.
Hijnen, D., et al., *J. Allergy Clin. Immunol. 113(2)*:334-40, 2004.
Hwang, S.T., *Adv. Dermatol. 17*:211-41, 2001.
Leung, D.Y., et al., *Lancet 361(9352)*: 151-60, 2003.
Lin, L., et al., *J. Med. Dent. Sci. 50(1)*:27-33, 2003.
Nagao, M., et al., *J. Allergy Clin. Immunol. 15(2)*:s272, 2005.
Matsuda, H., et al., *Int. Immunol. 9(3)*461-6, 1997.
Matsushima, H., et al., *J. Dermatol. Sci. 32(3)*:223-30, 2003.
Parrish-Novak, J.E., et al., Interleukin 31 is a novel four-helical-bundle cytokine that heterodimeric receptor complex expressed in epithelial cells of lung and skin, (1023) Annual Meeting of the American Society of Human Genetics, 2003.
Robert, C., et al., *N. Engl. J. Med. 341(24)*:1817-28, 1999.
Shimada, Y., et al., *J. Dermatol. Sci. 34(3)*:201-8, 2004.
Sonkoly, E., et al., *J. Allergy Clin. Immunol. 117(2)*:411-7, 2006.
Song, T., et al., *J. Allergy Clin. Immunol. 15(2)*:s100, 2005.
Takano, N., et al., *Eur. J. Pharmacol. 495(2-3)*:159-65, 2004.
Takano, N., et al., *Eur. J. Pharmacol. 471(3)*:223-8, 2003.
Takaoka, A., et al., *Exp. Dermatol. 15(3)*:161-7, 2006.
Takaoka, A., *Eur. J. Pharmacol.* PMID:15925362, 2005.
Vestergaard, C., et al., *J. Invest. Dermatol. 115(4)*:640-6, 2000.
GenBank Accession No. AI123586, 1997.
Gen Bank Accession No. AI799583, 1997.
CDTP64367599.
CDTP62671799.
Harlow et al., Ed. Antibodies, A Laboratory manual. Cold Spring Harbor Press. 1998, pp. 23-26.
Definition of "lichenification" in Stedman's Medical Dictionary, 27th Ed. (2000 Lippincott Williams & Wilkins).
Dillon et al., "Transgenic mice overexpressing a novel cytokine (IL-31) develop a severe pruritic skin phenotype resembling atopic dermatitis," European Cytokine Network 14(3): 81, 2003.
ExPASy Feature Aligner, Q8N17 (IL-31RA) human (accessed Nov. 11, 2007).
PFAM, FN3 (accessed Nov. 11, 2007).

\* cited by examiner

SEQUENCE LISTING

```
<160> NUMBER OF SEQ ID NOS: 20

<210> SEQ ID NO 1
<211> LENGTH: 495
<212> TYPE: DNA
<213> ORGANISM: Homo sapiens
<220> FEATURE:
<221> NAME/KEY: CDS
<222> LOCATION: (1)...(495)
<220> FEATURE:
<221> NAME/KEY: misc_feature
<222> LOCATION: (1)...(495)
<223> OTHER INFORMATION: human IL-31 ligand

<400> SEQUENCE: 1 atg gcc tct cac tca ggc ccc tcg acg tct gtg ctc ttt ctg ttc tgc      48
Met Ala Ser His Ser Gly Pro Ser Thr Ser Val Leu Phe Leu Phe Cys
 1               5                  10                  15 tgc ctg gga ggc tgg ctg gcc tcc cac acg ttg ccc gtc cgt tta cta      96
Cys Leu Gly Gly Trp Leu Ala Ser His Thr Leu Pro Val Arg Leu Leu
             20                  25                  30 cga cca agt gat gat gta cag aaa ata gtc gag gaa tta cag tcc ctc     144
Arg Pro Ser Asp Asp Val Gln Lys Ile Val Glu Glu Leu Gln Ser Leu
         35                  40                  45 tcg aag atg ctt ttg aaa gat gtg gag gaa gag aag ggc gtg ctc gtg     192
Ser Lys Met Leu Leu Lys Asp Val Glu Glu Glu Lys Gly Val Leu Val
     50                  55                  60 tcc cag aat tac acg ctg ccg tgt ctc agc cct gac gcc cag ccg cca     240
Ser Gln Asn Tyr Thr Leu Pro Cys Leu Ser Pro Asp Ala Gln Pro Pro
 65                  70                  75                  80 aac aac atc cac agc cca gcc atc cgg gca tat ctc aag aca atc aga     288
Asn Asn Ile His Ser Pro Ala Ile Arg Ala Tyr Leu Lys Thr Ile Arg
                 85                  90                  95 cag cta gac aac aaa tct gtt att gat gag atc ata gag cac ctc gac     336
Gln Leu Asp Asn Lys Ser Val Ile Asp Glu Ile Ile Glu His Leu Asp
            100                 105                 110 aaa ctc ata ttt caa gat gca cca gaa aca aac att tct gtg cca aca     384
Lys Leu Ile Phe Gln Asp Ala Pro Glu Thr Asn Ile Ser Val Pro Thr
        115                 120                 125 gac acc cat gaa tgt aaa cgc ttc atc ctg act att tct caa cag ttt     432
Asp Thr His Glu Cys Lys Arg Phe Ile Leu Thr Ile Ser Gln Gln Phe
    130                 135                 140 tca gag tgc atg gac ctc gca cta aaa tca ttg acc tct gga gcc caa     480
Ser Glu Cys Met Asp Leu Ala Leu Lys Ser Leu Thr Ser Gly Ala Gln
145                 150                 155                 160 cag gcc acc act taa                                                 495
Gln Ala Thr Thr *

<210> SEQ ID NO 2
<211> LENGTH: 164
<212> TYPE: PRT
<213> ORGANISM: Homo sapiens

<400> SEQUENCE: 2

Met Ala Ser His Ser Gly Pro Ser Thr Ser Val Leu Phe Leu Phe Cys
 1               5                  10                  15

Cys Leu Gly Gly Trp Leu Ala Ser His Thr Leu Pro Val Arg Leu Leu
```

```
                    20                  25                  30
Arg Pro Ser Asp Asp Val Gln Lys Ile Val Glu Glu Leu Gln Ser Leu
                35                  40                  45

Ser Lys Met Leu Leu Lys Asp Val Glu Glu Lys Gly Val Leu Val
         50                  55                  60

Ser Gln Asn Tyr Thr Leu Pro Cys Leu Ser Pro Asp Ala Gln Pro Pro
 65                  70                  75                  80

Asn Asn Ile His Ser Pro Ala Ile Arg Ala Tyr Leu Lys Thr Ile Arg
                 85                  90                  95

Gln Leu Asp Asn Lys Ser Val Ile Asp Glu Ile Ile Glu His Leu Asp
                100                 105                 110

Lys Leu Ile Phe Gln Asp Ala Pro Glu Thr Asn Ile Ser Val Pro Thr
            115                 120                 125

Asp Thr His Glu Cys Lys Arg Phe Ile Leu Thr Ile Ser Gln Gln Phe
        130                 135                 140

Ser Glu Cys Met Asp Leu Ala Leu Lys Ser Leu Thr Ser Gly Ala Gln
145                 150                 155                 160

Gln Ala Thr Thr

<210> SEQ ID NO 3
<211> LENGTH: 492
<212> TYPE: DNA
<213> ORGANISM: Mus musculus
<220> FEATURE:
<221> NAME/KEY: CDS
<222> LOCATION: (1)...(492)
<220> FEATURE:
<221> NAME/KEY: misc_feature
<222> LOCATION: (1)...(492)
<223> OTHER INFORMATION: mouse IL-31 ligand

<400> SEQUENCE: 3 atg atc ttc cac aca gga aca acg aag cct acc ctg gtg ctg ctt tgc    48
Met Ile Phe His Thr Gly Thr Thr Lys Pro Thr Leu Val Leu Leu Cys
  1               5                  10                  15 tgt ata gga acc tgg ctg gcc acc tgc agc ttg tcc ttc ggt gcc cca    96
Cys Ile Gly Thr Trp Leu Ala Thr Cys Ser Leu Ser Phe Gly Ala Pro
                 20                  25                  30 ata tcg aag gaa gac tta aga act aca att gac ctc ttg aaa caa gag   144
Ile Ser Lys Glu Asp Leu Arg Thr Thr Ile Asp Leu Leu Lys Gln Glu
             35                  40                  45 tct cag gat ctt tat aac aac tat agc ata aag cag gca tct ggg atg   192
Ser Gln Asp Leu Tyr Asn Asn Tyr Ser Ile Lys Gln Ala Ser Gly Met
         50                  55                  60 tca gca gac gaa tca ata cag ctg ccg tgt ttc agc ctg gac cgg gaa   240
Ser Ala Asp Glu Ser Ile Gln Leu Pro Cys Phe Ser Leu Asp Arg Glu
 65                  70                  75                  80 gca tta acc aac atc tcg gtc atc ata gca cat ctg gag aaa gtc aaa   288
Ala Leu Thr Asn Ile Ser Val Ile Ile Ala His Leu Glu Lys Val Lys
                 85                  90                  95 gtg ttg agc gag aac aca gta gat act tct tgg gtg ata aga tgg cta   336
Val Leu Ser Glu Asn Thr Val Asp Thr Ser Trp Val Ile Arg Trp Leu
            100                 105                 110 aca aac atc agc tgt ttc aac cca ctg aat tta aac att tct gtg cct   384
Thr Asn Ile Ser Cys Phe Asn Pro Leu Asn Leu Asn Ile Ser Val Pro
        115                 120                 125 gga aat act gat gaa tcc tat gat tgt aaa gtg ttc gtg ctt acg gtt   432
Gly Asn Thr Asp Glu Ser Tyr Asp Cys Lys Val Phe Val Leu Thr Val
        130                 135                 140
```

-continued

```
tta aag cag ttc tca aac tgc atg gca gaa ctg cag gct aag gac aat    480
Leu Lys Gln Phe Ser Asn Cys Met Ala Glu Leu Gln Ala Lys Asp Asn
145                 150                 155                 160 act aca tgc tga                                                    492
Thr Thr Cys *

<210> SEQ ID NO 4
<211> LENGTH: 163
<212> TYPE: PRT
<213> ORGANISM: Mus musculus

<400> SEQUENCE: 4

Met Ile Phe His Thr Gly Thr Thr Lys Pro Thr Leu Val Leu Leu Cys
1               5                   10                  15

Cys Ile Gly Thr Trp Leu Ala Thr Cys Ser Leu Ser Phe Gly Ala Pro
                20                  25                  30

Ile Ser Lys Glu Asp Leu Arg Thr Ile Asp Leu Leu Lys Gln Glu
        35                  40                  45

Ser Gln Asp Leu Tyr Asn Asn Tyr Ser Ile Lys Gln Ala Ser Gly Met
    50                  55                  60

Ser Ala Asp Glu Ser Ile Gln Leu Pro Cys Phe Ser Leu Asp Arg Glu
65                  70                  75                  80

Ala Leu Thr Asn Ile Ser Val Ile Ala His Leu Glu Lys Val Lys
                85                  90                  95

Val Leu Ser Glu Asn Thr Val Asp Thr Ser Trp Val Ile Arg Trp Leu
                100                 105                 110

Thr Asn Ile Ser Cys Phe Asn Pro Leu Asn Leu Asn Ile Ser Val Pro
            115                 120                 125

Gly Asn Thr Asp Glu Ser Tyr Asp Cys Lys Val Phe Val Leu Thr Val
        130                 135                 140

Leu Lys Gln Phe Ser Asn Cys Met Ala Glu Leu Gln Ala Lys Asp Asn
145                 150                 155                 160

Thr Thr Cys

<210> SEQ ID NO 5
<211> LENGTH: 2199
<212> TYPE: DNA
<213> ORGANISM: Homo sapiens
<220> FEATURE:
<221> NAME/KEY: CDS
<222> LOCATION: (1)...(2199)
<220> FEATURE:
<221> NAME/KEY: misc_feature
<222> LOCATION: (1)...(2199)
<223> OTHER INFORMATION: IL-31RA "long" form

<400> SEQUENCE: 5 atg atg tgg acc tgg gca ctg tgg atg ctc ccc tca ctc tgc aaa ttc    48
Met Met Trp Thr Trp Ala Leu Trp Met Leu Pro Ser Leu Cys Lys Phe
1               5                   10                  15 agc ctg gca gct ctg cca gct aag cct gag aac att tcc tgt gtc tac    96
Ser Leu Ala Ala Leu Pro Ala Lys Pro Glu Asn Ile Ser Cys Val Tyr
                20                  25                  30 tac tat agg aaa aat tta acc tgc act tgg agt cca gga aag gaa acc    144
Tyr Tyr Arg Lys Asn Leu Thr Cys Thr Trp Ser Pro Gly Lys Glu Thr
        35                  40                  45 agt tat acc cag tac aca gtt aag aga act tac gct ttt gga gaa aaa    192
Ser Tyr Thr Gln Tyr Thr Val Lys Arg Thr Tyr Ala Phe Gly Glu Lys
    50                  55                  60 cat gat aat tgt aca acc aat agt tct aca gtg aaa atc gtg ctt cg    240
```

```
                His Asp Asn Cys Thr Thr Asn Ser Ser Thr Ser Glu Asn Arg Ala Ser
                 65                  70                  75                  80 tgc tct ttt ttc ctt cca aga ata acg atc cca gat aat tat acc att              288
Cys Ser Phe Phe Leu Pro Arg Ile Thr Ile Pro Asp Asn Tyr Thr Ile
                     85                  90                  95 gag gtg gaa gct gaa aat gga gat ggt gta att aaa tct cat atg aca              336
Glu Val Glu Ala Glu Asn Gly Asp Gly Val Ile Lys Ser His Met Thr
                100                 105                 110 tac tgg aga tta gag aac ata gcg aaa act gaa cca cct aag att ttc              384
Tyr Trp Arg Leu Glu Asn Ile Ala Lys Thr Glu Pro Pro Lys Ile Phe
            115                 120                 125 cgt gtg aaa cca gtt ttg ggc atc aaa cga atg att caa att gaa tgg              432
Arg Val Lys Pro Val Leu Gly Ile Lys Arg Met Ile Gln Ile Glu Trp
        130                 135                 140 ata aag cct gag ttg gcg cct gtt tca tct gat tta aaa tac aca ctt              480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct              528
Arg Phe Arg Thr Val Asn Ser Thr Ser Trp Met Glu Val Asn Phe Ala
                165                 170                 175 aag aac cgt aag gat aaa aac caa acg tac aac ctc acg ggg ctg cag              576
Lys Asn Arg Lys Asp Lys Asn Gln Thr Tyr Asn Leu Thr Gly Leu Gln
            180                 185                 190 cct ttt aca gaa tat gtc ata gct ctg cga tgt gcg gtc aag gag tca              624
Pro Phe Thr Glu Tyr Val Ile Ala Leu Arg Cys Ala Val Lys Glu Ser
        195                 200                 205 aag ttc tgg agt gac tgg agc caa gaa aaa atg gga atg act gag gaa              672
Lys Phe Trp Ser Asp Trp Ser Gln Glu Lys Met Gly Met Thr Glu Glu
210                 215                 220 gaa gct cca tgt ggc ctg gaa ctg tgg aga gtc ctg aaa cca gct gag              720
Glu Ala Pro Cys Gly Leu Glu Leu Trp Arg Val Leu Lys Pro Ala Glu
225                 230                 235                 240 gcg gat gga aga agg cca gtg cgg ttg tta tgg aag aag gca aga gga              768
Ala Asp Gly Arg Arg Pro Val Arg Leu Leu Trp Lys Lys Ala Arg Gly
                245                 250                 255 gcc cca gtc cta gag aaa aca ctt ggc tac aac ata tgg tac tat cca              816
Ala Pro Val Leu Glu Lys Thr Leu Gly Tyr Asn Ile Trp Tyr Tyr Pro
            260                 265                 270 gaa agc aac act aac ctc aca gaa aca atg aac act act aac cag cag              864
Glu Ser Asn Thr Asn Leu Thr Glu Thr Met Asn Thr Thr Asn Gln Gln
        275                 280                 285 ctt gaa ctg cat ctg gga ggc gag agc ttt tgg gtg tct atg att tct              912
Leu Glu Leu His Leu Gly Gly Glu Ser Phe Trp Val Ser Met Ile Ser
    290                 295                 300 tat aat tct ctt ggg aag tct cca gtg gcc acc ctg agg att cca gct              960
Tyr Asn Ser Leu Gly Lys Ser Pro Val Ala Thr Leu Arg Ile Pro Ala
305                 310                 315                 320 att caa gaa aaa tca ttt cag tgc att gag gtc atg cag gcc tgc gtt             1008
Ile Gln Glu Lys Ser Phe Gln Cys Ile Glu Val Met Gln Ala Cys Val
                325                 330                 335 gct gag gac cag cta gtg gtg aag tgg caa agc tct gct cta gac gtg             1056
Ala Glu Asp Gln Leu Val Val Lys Trp Gln Ser Ser Ala Leu Asp Val
            340                 345                 350 aac act tgg atg att gaa tgg ttt ccg gat gtg gac tca gag ccc acc             1104
Asn Thr Trp Met Ile Glu Trp Phe Pro Asp Val Asp Ser Glu Pro Thr
        355                 360                 365 acc ctt tcc tgg gaa tct gtg tct cag gcc acg aac tgg acg atc cag             1152
Thr Leu Ser Trp Glu Ser Val Ser Gln Ala Thr Asn Trp Thr Ile Gln
    370                 375                 380
```

-continued

```
caa gat aaa tta aaa cct ttc tgg tgc tat aac atc tct gtg tat cca    1200
Gln Asp Lys Leu Lys Pro Phe Trp Cys Tyr Asn Ile Ser Val Tyr Pro
385                 390                 395                 400 atg ttg cat gac aaa gtt ggc gag cca tat tcc atc cag gct tat gcc    1248
Met Leu His Asp Lys Val Gly Glu Pro Tyr Ser Ile Gln Ala Tyr Ala
            405                 410                 415 aaa gaa ggc gtt cca tca gaa ggt cct gag acc aag gtg gag aac att    1296
Lys Glu Gly Val Pro Ser Glu Gly Pro Glu Thr Lys Val Glu Asn Ile
        420                 425                 430 ggc gtg aag acg gtc acg atc aca tgg aaa gag att ccc aag agt gag    1344
Gly Val Lys Thr Val Thr Ile Thr Trp Lys Glu Ile Pro Lys Ser Glu
    435                 440                 445 aga aag ggt atc atc tgc aac tac acc atc ttt tac caa gct gaa ggt    1392
Arg Lys Gly Ile Ile Cys Asn Tyr Thr Ile Phe Tyr Gln Ala Glu Gly
450                 455                 460 gga aaa gga ttc tcc aag aca gtc aat tcc agc atc ttg cag tac ggc    1440
Gly Lys Gly Phe Ser Lys Thr Val Asn Ser Ser Ile Leu Gln Tyr Gly
465                 470                 475                 480 ctg gag tcc ctg aaa cga aag acc tct tac att gtt cag gtc atg gcc    1488
Leu Glu Ser Leu Lys Arg Lys Thr Ser Tyr Ile Val Gln Val Met Ala
            485                 490                 495 agc acc agt gct ggg gga acc aac ggg acc agc ata aat ttc aag aca    1536
Ser Thr Ser Ala Gly Gly Thr Asn Gly Thr Ser Ile Asn Phe Lys Thr
        500                 505                 510 ttg tca ttc agt gtc ttt gag att atc ctc ata act tct ctg att ggt    1584
Leu Ser Phe Ser Val Phe Glu Ile Ile Leu Ile Thr Ser Leu Ile Gly
    515                 520                 525 gga ggc ctt ctt att ctc att atc ctg aca gtg gca tat ggt ctc aaa    1632
Gly Gly Leu Leu Ile Leu Ile Ile Leu Thr Val Ala Tyr Gly Leu Lys
530                 535                 540 aaa ccc aac aaa ttg act cat ctg tgt tgg ccc acc gtt ccc aac cct    1680
Lys Pro Asn Lys Leu Thr His Leu Cys Trp Pro Thr Val Pro Asn Pro
545                 550                 555                 560 gct gaa agt agt ata gcc aca tgg cat gga gat gat ttc aag gat aag    1728
Ala Glu Ser Ser Ile Ala Thr Trp His Gly Asp Asp Phe Lys Asp Lys
            565                 570                 575 cta aac ctg aag gag tct gat gac tct gtg aac aca gaa gac agg atc    1776
Leu Asn Leu Lys Glu Ser Asp Asp Ser Val Asn Thr Glu Asp Arg Ile
        580                 585                 590 tta aaa cca tgt tcc acc ccc agt gac aag ttg gtg att gac aag ttg    1824
Leu Lys Pro Cys Ser Thr Pro Ser Asp Lys Leu Val Ile Asp Lys Leu
    595                 600                 605 gtg gtg aac ttt ggg aat gtt ctg caa gaa att ttc aca gat gaa gcc    1872
Val Val Asn Phe Gly Asn Val Leu Gln Glu Ile Phe Thr Asp Glu Ala
610                 615                 620 aga acg ggt cag gaa aac aat tta gga ggg gaa aag aat ggg tat gtg    1920
Arg Thr Gly Gln Glu Asn Asn Leu Gly Gly Glu Lys Asn Gly Tyr Val
625                 630                 635                 640 acc tgc ccc ttc agg cct gat tgt ccc ctg ggg aaa agt ttt gag gag    1968
Thr Cys Pro Phe Arg Pro Asp Cys Pro Leu Gly Lys Ser Phe Glu Glu
            645                 650                 655 ctc cca gtt tca cct gag att ccg ccc aga aaa tcc caa tac cta cgt    2016
Leu Pro Val Ser Pro Glu Ile Pro Pro Arg Lys Ser Gln Tyr Leu Arg
        660                 665                 670 tcg agg atg cca gag ggg acc cgc cca gaa gcc aaa gag cag ctt ctc    2064
Ser Arg Met Pro Glu Gly Thr Arg Pro Glu Ala Lys Glu Gln Leu Leu
    675                 680                 685 ttt tct ggt caa agt tta gta cca gat cat ctg tgt gag gaa gga gcc    2112
Phe Ser Gly Gln Ser Leu Val Pro Asp His Leu Cys Glu Glu Gly Ala
690                 695                 700
```

-continued

```
cca aat cca tat ttg aaa aat tca gtg aca gcc agg gaa ttt ctt gtg    2160
Pro Asn Pro Tyr Leu Lys Asn Ser Val Thr Ala Arg Glu Phe Leu Val
705             710                 715                 720 tct gaa aaa ctt cca gag cac acc aag gga gaa gtc taa                2199
Ser Glu Lys Leu Pro Glu His Thr Lys Gly Glu Val *
                725                 730
```

<210> SEQ ID NO 6
<211> LENGTH: 732
<212> TYPE: PRT
<213> ORGANISM: Homo sapiens

<400> SEQUENCE: 6

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
                20                  25                  30

Tyr Tyr Arg Lys Asn Leu Thr Cys Thr Trp Ser Pro Gly Lys Glu Thr
            35                  40                  45

Ser Tyr Thr Gln Tyr Thr Val Lys Arg Thr Tyr Ala Phe Gly Glu Lys
        50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335
```

```
Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
            355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
            405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
            435                 440                 445

Arg Lys Gly Ile Ile Cys Asn Tyr Thr Ile Phe Tyr Gln Ala Glu Gly
        450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
            485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
        530                 535                 540

Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
            565                 570                 575

Leu Asn Leu Lys Glu Ser Asp Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
        610                 615                 620

Arg Thr Gly Gln Glu Asn Asn Leu Gly Gly Glu Lys Asn Gly Tyr Val
625                 630                 635                 640

Thr Cys Pro Phe Arg Pro Asp Cys Pro Leu Gly Lys Ser Phe Glu Glu
            645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
        690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
            725                 730

<210> SEQ ID NO 7
<211> LENGTH: 1989
```

```
<212> TYPE: DNA
<213> ORGANISM: Homo sapiens
<220> FEATURE:
<221> NAME/KEY: CDS
<222> LOCATION: (1)...(1989)
<220> FEATURE:
<221> NAME/KEY: misc_feature
<222> LOCATION: (1)...(1989)
<223> OTHER INFORMATION: IL-31RA "short" form

<400> SEQUENCE: 7 atg aag ctc tct ccc cag cct tca tgt gtt aac ctg ggg atg atg tgg      48
Met Lys Leu Ser Pro Gln Pro Ser Cys Val Asn Leu Gly Met Met Trp
 1               5                  10                  15 acc tgg gca ctg tgg atg ctc cct tca ctc tgc aaa ttc agc ctg gca      96
Thr Trp Ala Leu Trp Met Leu Pro Ser Leu Cys Lys Phe Ser Leu Ala
                20                  25                  30 gct ctg cca gct aag cct gag aac att tcc tgt gtc tac tac tat agg     144
Ala Leu Pro Ala Lys Pro Glu Asn Ile Ser Cys Val Tyr Tyr Tyr Arg
            35                  40                  45 aaa aat tta acc tgc act tgg agt cca gga aag gaa acc agt tat acc     192
Lys Asn Leu Thr Cys Thr Trp Ser Pro Gly Lys Glu Thr Ser Tyr Thr
 50                  55                  60 cag tac aca gtt aag aga act tac gct ttt gga gaa aaa cat gat aat     240
Gln Tyr Thr Val Lys Arg Thr Tyr Ala Phe Gly Glu Lys His Asp Asn
 65                  70                  75                  80 tgt aca acc aat agt tct aca agt gaa aat cgt gct tcg tgc tct ttt     288
Cys Thr Thr Asn Ser Ser Thr Ser Glu Asn Arg Ala Ser Cys Ser Phe
                 85                  90                  95 ttc ctt cca aga ata acg atc cca gat aat tat acc att gag gtg gaa     336
Phe Leu Pro Arg Ile Thr Ile Pro Asp Asn Tyr Thr Ile Glu Val Glu
            100                 105                 110 gct gaa aat gga gat ggt gta att aaa tct cat atg aca tac tgg aga     384
Ala Glu Asn Gly Asp Gly Val Ile Lys Ser His Met Thr Tyr Trp Arg
        115                 120                 125 tta gag aac ata gcg aaa act gaa cca cct aag att ttc cgt gtg aaa     432
Leu Glu Asn Ile Ala Lys Thr Glu Pro Pro Lys Ile Phe Arg Val Lys
    130                 135                 140 cca gtt ttg ggc atc aaa cga atg att caa att gaa tgg ata aag cct     480
Pro Val Leu Gly Ile Lys Arg Met Ile Gln Ile Glu Trp Ile Lys Pro
145                 150                 155                 160 gag ttg gcg cct gtt tca tct gat tta aaa tac aca ctt cga ttc agg     528
Glu Leu Ala Pro Val Ser Ser Asp Leu Lys Tyr Thr Leu Arg Phe Arg
                165                 170                 175 aca gtc aac agt acc agc tgg atg gaa gtc aac ttc gct aag aac cgt     576
Thr Val Asn Ser Thr Ser Trp Met Glu Val Asn Phe Ala Lys Asn Arg
            180                 185                 190 aag gat aaa aac caa acg tac aac ctc acg ggg ctg cag cct ttt aca     624
Lys Asp Lys Asn Gln Thr Tyr Asn Leu Thr Gly Leu Gln Pro Phe Thr
        195                 200                 205 gaa tat gtc ata gct ctg cga tgt gcg gtc aag gag tca aag ttc tgg     672
Glu Tyr Val Ile Ala Leu Arg Cys Ala Val Lys Glu Ser Lys Phe Trp
    210                 215                 220 agt gac tgg agc caa gaa aaa atg gga atg act gag gaa gaa gct cca     720
Ser Asp Trp Ser Gln Glu Lys Met Gly Met Thr Glu Glu Glu Ala Pro
225                 230                 235                 240 tgt ggc ctg gaa ctg tgg aga gtc ctg aaa cca gct gag gcg gat gga     768
Cys Gly Leu Glu Leu Trp Arg Val Leu Lys Pro Ala Glu Ala Asp Gly
                245                 250                 255 aga agg cca gtg cgg ttg tta tgg aag aag gca aga gga gcc cca gtc     816
Arg Arg Pro Val Arg Leu Leu Trp Lys Lys Ala Arg Gly Ala Pro Val
            260                 265                 270
```

-continued

| | |
|---|---|
| cta gag aaa aca ctt ggc tac aac ata tgg tac tat cca gaa agc aac<br>Leu Glu Lys Thr Leu Gly Tyr Asn Ile Trp Tyr Tyr Pro Glu Ser Asn<br>              275                  280                  285 | 864 |
| act aac ctc aca gaa aca atg aac act act aac cag cag ctt gaa ctg<br>Thr Asn Leu Thr Glu Thr Met Asn Thr Thr Asn Gln Gln Leu Glu Leu<br>    290                  295                  300 | 912 |
| cat ctg gga ggc gag agc ttt tgg gtg tct atg att tct tat aat tct<br>His Leu Gly Gly Glu Ser Phe Trp Val Ser Met Ile Ser Tyr Asn Ser<br>305                  310                  315                  320 | 960 |
| ctt ggg aag tct cca gtg gcc acc ctg agg att cca gct att caa gaa<br>Leu Gly Lys Ser Pro Val Ala Thr Leu Arg Ile Pro Ala Ile Gln Glu<br>              325                  330                  335 | 1008 |
| aaa tca ttt cag tgc att gag gtc atg cag gcc tgc gtt gct gag gac<br>Lys Ser Phe Gln Cys Ile Glu Val Met Gln Ala Cys Val Ala Glu Asp<br>    340                  345                  350 | 1056 |
| cag cta gtg gtg aag tgg caa agc tct gct cta gac gtg aac act tgg<br>Gln Leu Val Val Lys Trp Gln Ser Ser Ala Leu Asp Val Asn Thr Trp<br>              355                  360                  365 | 1104 |
| atg att gaa tgg ttt ccg gat gtg gac tca gag ccc acc acc ctt tcc<br>Met Ile Glu Trp Phe Pro Asp Val Asp Ser Glu Pro Thr Thr Leu Ser<br>    370                  375                  380 | 1152 |
| tgg gaa tct gtg tct cag gcc acg aac tgg acg atc cag caa gat aaa<br>Trp Glu Ser Val Ser Gln Ala Thr Asn Trp Thr Ile Gln Gln Asp Lys<br>385                  390                  395                  400 | 1200 |
| tta aaa cct ttc tgg tgc tat aac atc tct gtg tat cca atg ttg cat<br>Leu Lys Pro Phe Trp Cys Tyr Asn Ile Ser Val Tyr Pro Met Leu His<br>              405                  410                  415 | 1248 |
| gac aaa gtt ggc gag cca tat tcc atc cag gct tat gcc aaa gaa ggc<br>Asp Lys Val Gly Glu Pro Tyr Ser Ile Gln Ala Tyr Ala Lys Glu Gly<br>    420                  425                  430 | 1296 |
| gtt cca tca gaa ggt cct gag acc aag gtg gag aac att ggc gtg aag<br>Val Pro Ser Glu Gly Pro Glu Thr Lys Val Glu Asn Ile Gly Val Lys<br>              435                  440                  445 | 1344 |
| acg gtc acg atc aca tgg aaa gag att ccc aag agt gag aga aag ggt<br>Thr Val Thr Ile Thr Trp Lys Glu Ile Pro Lys Ser Glu Arg Lys Gly<br>    450                  455                  460 | 1392 |
| atc atc tgc aac tac acc atc ttt tac caa gct gaa ggt gga aaa gga<br>Ile Ile Cys Asn Tyr Thr Ile Phe Tyr Gln Ala Glu Gly Gly Lys Gly<br>465                  470                  475                  480 | 1440 |
| ttc tcc aag aca gtc aat tcc agc atc ttg cag tac ggc ctg gag tcc<br>Phe Ser Lys Thr Val Asn Ser Ser Ile Leu Gln Tyr Gly Leu Glu Ser<br>              485                  490                  495 | 1488 |
| ctg aaa cga aag acc tct tac att gtt cag gtc atg gcc agc acc agt<br>Leu Lys Arg Lys Thr Ser Tyr Ile Val Gln Val Met Ala Ser Thr Ser<br>            500                  505                  510 | 1536 |
| gct ggg gga acc aac ggg acc agc ata aat ttc aag aca ttg tca ttc<br>Ala Gly Gly Thr Asn Gly Thr Ser Ile Asn Phe Lys Thr Leu Ser Phe<br>              515                  520                  525 | 1584 |
| agt gtc ttt gag att atc ctc ata act tct ctg att ggt gga ggc ctt<br>Ser Val Phe Glu Ile Ile Leu Ile Thr Ser Leu Ile Gly Gly Gly Leu<br>    530                  535                  540 | 1632 |
| ctt att ctc att atc ctg aca gtg gca tat ggt ctc aaa aaa ccc aac<br>Leu Ile Leu Ile Ile Leu Thr Val Ala Tyr Gly Leu Lys Lys Pro Asn<br>545                  550                  555                  560 | 1680 |
| aaa ttg act cat ctg tgt tgg ccc acc gtt ccc aac cct gct gaa agt<br>Lys Leu Thr His Leu Cys Trp Pro Thr Val Pro Asn Pro Ala Glu Ser<br>              565                  570                  575 | 1728 |
| agt ata gcc aca tgg cat gga gat gat ttc aag gat aag cta aac ctg<br>Ser Ile Ala Thr Trp His Gly Asp Asp Phe Lys Asp Lys Leu Asn Leu | 1776 |

-continued

```
                 580                 585                 590
aag gag tct gat gac tct gtg aac aca gaa gac agg atc tta aaa cca    1824
Lys Glu Ser Asp Asp Ser Val Asn Thr Glu Asp Arg Ile Leu Lys Pro
             595                 600                 605 tgt tcc acc ccc agt gac aag ttg gtg att gac aag ttg gtg gtg aac    1872
Cys Ser Thr Pro Ser Asp Lys Leu Val Ile Asp Lys Leu Val Val Asn
        610                 615                 620 ttt ggg aat gtt ctg caa gaa att ttc aca gat gaa gcc aga acg ggt    1920
Phe Gly Asn Val Leu Gln Glu Ile Phe Thr Asp Glu Ala Arg Thr Gly
625                 630                 635                 640 cag gaa aac aat tta gga ggg gaa aag aat ggg act aga att ctg tct    1968
Gln Glu Asn Asn Leu Gly Gly Glu Lys Asn Gly Thr Arg Ile Leu Ser
                645                 650                 655 tcc tgc cca act tca ata taa                                        1989
Ser Cys Pro Thr Ser Ile *
            660
```

<210> SEQ ID NO 8
<211> LENGTH: 662
<212> TYPE: PRT
<213> ORGANISM: Homo sapiens

<400> SEQUENCE: 8

```
Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
```

```
              260                 265                 270
Leu Glu Lys Thr Leu Gly Tyr Asn Ile Trp Tyr Tyr Pro Glu Ser Asn
            275                 280                 285

Thr Asn Leu Thr Glu Thr Met Asn Thr Thr Asn Gln Gln Leu Glu Leu
        290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Pro Thr Thr Leu Ser
370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
                420                 425                 430

Val Pro Ser Glu Gly Pro Glu Thr Lys Val Glu Asn Ile Gly Val Lys
            435                 440                 445

Thr Val Thr Ile Thr Trp Lys Glu Ile Pro Lys Ser Glu Arg Lys Gly
        450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
                500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
            595                 600                 605

Cys Ser Thr Pro Ser Asp Lys Leu Val Ile Asp Lys Leu Val Val Asn
        610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
                660

<210> SEQ ID NO 9
```

<211> LENGTH: 975
<212> TYPE: DNA
<213> ORGANISM: Homo sapiens
<220> FEATURE:
<221> NAME/KEY: CDS
<222> LOCATION: (1)...(975)
<220> FEATURE:
<221> NAME/KEY: misc_feature
<222> LOCATION: (1)...(975)
<223> OTHER INFORMATION: soluble IL-31RA "long" form

<400> SEQUENCE: 9

| | | | | | | | | | | | | | | | | |
|---|---|---|---|---|---|---|---|---|---|---|---|---|---|---|---|---|
| atg | atg | tgg | acc | tgg | gca | ctg | tgg | atg | ctc | ccc | tca | ctc | tgc | aaa | ttc | 48 |
| Met | Met | Trp | Thr | Trp | Ala | Leu | Trp | Met | Leu | Pro | Ser | Leu | Cys | Lys | Phe | |
| 1 | | | | 5 | | | | | 10 | | | | | 15 | | |
| agc | ctg | gca | gct | ctg | cca | gct | aag | cct | gag | aac | att | tcc | tgt | gtc | tac | 96 |
| Ser | Leu | Ala | Ala | Leu | Pro | Ala | Lys | Pro | Glu | Asn | Ile | Ser | Cys | Val | Tyr | |
| | | 20 | | | | | 25 | | | | | 30 | | | | |
| tac | tat | agg | aaa | aat | tta | acc | tgc | act | tgg | agt | cca | gga | aag | gaa | acc | 144 |
| Tyr | Tyr | Arg | Lys | Asn | Leu | Thr | Cys | Thr | Trp | Ser | Pro | Gly | Lys | Glu | Thr | |
| | | 35 | | | | | 40 | | | | | 45 | | | | |
| agt | tat | acc | cag | tac | aca | gtt | aag | aga | act | tac | gct | ttt | gga | gaa | aaa | 192 |
| Ser | Tyr | Thr | Gln | Tyr | Thr | Val | Lys | Arg | Thr | Tyr | Ala | Phe | Gly | Glu | Lys | |
| 50 | | | | | 55 | | | | | 60 | | | | | | |
| cat | gat | aat | tgt | aca | acc | aat | agt | tct | aca | agt | gaa | aat | cgt | gct | tcg | 240 |
| His | Asp | Asn | Cys | Thr | Thr | Asn | Ser | Ser | Thr | Ser | Glu | Asn | Arg | Ala | Ser | |
| 65 | | | | | 70 | | | | | 75 | | | | | 80 | |
| tgc | tct | ttt | ttc | ctt | cca | aga | ata | acg | atc | cca | gat | aat | tat | acc | att | 288 |
| Cys | Ser | Phe | Phe | Leu | Pro | Arg | Ile | Thr | Ile | Pro | Asp | Asn | Tyr | Thr | Ile | |
| | | | | 85 | | | | | 90 | | | | | 95 | | |
| gag | gtg | gaa | gct | gaa | aat | gga | gat | ggt | gta | att | aaa | tct | cat | atg | aca | 336 |
| Glu | Val | Glu | Ala | Glu | Asn | Gly | Asp | Gly | Val | Ile | Lys | Ser | His | Met | Thr | |
| | | | | 100 | | | | | 105 | | | | | 110 | | |
| tac | tgg | aga | tta | gag | aac | ata | gcg | aaa | act | gaa | cca | cct | aag | att | ttc | 384 |
| Tyr | Trp | Arg | Leu | Glu | Asn | Ile | Ala | Lys | Thr | Glu | Pro | Pro | Lys | Ile | Phe | |
| | | 115 | | | | | 120 | | | | | 125 | | | | |
| cgt | gtg | aaa | cca | gtt | ttg | ggc | atc | aaa | cga | atg | att | caa | att | gaa | tgg | 432 |
| Arg | Val | Lys | Pro | Val | Leu | Gly | Ile | Lys | Arg | Met | Ile | Gln | Ile | Glu | Trp | |
| | | 130 | | | | | 135 | | | | | 140 | | | | |
| ata | aag | cct | gag | ttg | gcg | cct | gtt | tca | tct | gat | tta | aaa | tac | aca | ctt | 480 |
| Ile | Lys | Pro | Glu | Leu | Ala | Pro | Val | Ser | Ser | Asp | Leu | Lys | Tyr | Thr | Leu | |
| 145 | | | | | 150 | | | | | 155 | | | | | 160 | |
| cga | ttc | agg | aca | gtc | aac | agt | acc | agc | tgg | atg | gaa | gtc | aac | ttc | gct | 528 |
| Arg | Phe | Arg | Thr | Val | Asn | Ser | Thr | Ser | Trp | Met | Glu | Val | Asn | Phe | Ala | |
| | | | | 165 | | | | | 170 | | | | | 175 | | |
| aag | aac | cgt | aag | gat | aaa | aac | caa | acg | tac | aac | ctc | acg | ggg | ctg | cag | 576 |
| Lys | Asn | Arg | Lys | Asp | Lys | Asn | Gln | Thr | Tyr | Asn | Leu | Thr | Gly | Leu | Gln | |
| | | | | 180 | | | | | 185 | | | | | 190 | | |
| cct | ttt | aca | gaa | tat | gtc | ata | gct | ctg | cga | tgt | gcg | gtc | aag | gag | tca | 624 |
| Pro | Phe | Thr | Glu | Tyr | Val | Ile | Ala | Leu | Arg | Cys | Ala | Val | Lys | Glu | Ser | |
| | | 195 | | | | | 200 | | | | | 205 | | | | |
| aag | ttc | tgg | agt | gac | tgg | agc | caa | gaa | aaa | atg | gga | atg | act | gag | gaa | 672 |
| Lys | Phe | Trp | Ser | Asp | Trp | Ser | Gln | Glu | Lys | Met | Gly | Met | Thr | Glu | Glu | |
| | | 210 | | | | | 215 | | | | | 220 | | | | |
| gaa | gct | cca | tgt | ggc | ctg | gaa | ctg | tgg | aga | gtc | ctg | aaa | cca | gct | gag | 720 |
| Glu | Ala | Pro | Cys | Gly | Leu | Glu | Leu | Trp | Arg | Val | Leu | Lys | Pro | Ala | Glu | |
| 225 | | | | | 230 | | | | | 235 | | | | | 240 | |
| gcg | gat | gga | aga | agg | cca | gtg | cgg | ttg | tta | tgg | aag | aag | gca | aga | gga | 768 |
| Ala | Asp | Gly | Arg | Arg | Pro | Val | Arg | Leu | Leu | Trp | Lys | Lys | Ala | Arg | Gly | |
| | | | | 245 | | | | | 250 | | | | | 255 | | |
| gcc | cca | gtc | cta | gag | aaa | aca | ctt | ggc | tac | aac | ata | tgg | tac | tat | cca | 816 |
| Ala | Pro | Val | Leu | Glu | Lys | Thr | Leu | Gly | Tyr | Asn | Ile | Trp | Tyr | Tyr | Pro | |

```
                       260                 265                 270
gaa agc aac act aac ctc aca gaa aca atg aac act act aac cag cag       864
Glu Ser Asn Thr Asn Leu Thr Glu Thr Met Asn Thr Thr Asn Gln Gln
        275                 280                 285 ctt gaa ctg cat ctg gga ggc gag agc ttt tgg gtg tct atg att tct       912
Leu Glu Leu His Leu Gly Gly Glu Ser Phe Trp Val Ser Met Ile Ser
290                 295                 300 tat aat tct ctt ggg aag tct cca gtg gcc acc ctg agg att cca gct       960
Tyr Asn Ser Leu Gly Lys Ser Pro Val Ala Thr Leu Arg Ile Pro Ala
305                 310                 315                 320 att caa gaa aaa tag                                                   975
Ile Gln Glu Lys *
```

<210> SEQ ID NO 10
<211> LENGTH: 324
<212> TYPE: PRT
<213> ORGANISM: Homo sapiens

<400> SEQUENCE: 10

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285
```

```
Leu Glu Leu His Leu Gly Gly Glu Ser Phe Trp Val Ser Met Ile Ser
    290                 295                 300
Tyr Asn Ser Leu Gly Lys Ser Pro Val Ala Thr Leu Arg Ile Pro Ala
305                 310                 315                 320
Ile Gln Glu Lys

<210> SEQ ID NO 11
<211> LENGTH: 720
<212> TYPE: DNA
<213> ORGANISM: Homo sapiens
<220> FEATURE:
<221> NAME/KEY: CDS
<222> LOCATION: (1)...(720)
<220> FEATURE:
<221> NAME/KEY: misc_feature
<222> LOCATION: (1)...(720)
<223> OTHER INFORMATION: soluble IL-31RA "short" form

<400> SEQUENCE: 11 atg atg tgg acc tgg gca ctg tgg atg ctc ccc tca ctc tgc aaa ttc     48
Met Met Trp Thr Trp Ala Leu Trp Met Leu Pro Ser Leu Cys Lys Phe
 1               5                  10                  15 agc ctg gca gct ctg cca gct aag cct gag aac att tcc tgt gtc tac     96
Ser Leu Ala Ala Leu Pro Ala Lys Pro Glu Asn Ile Ser Cys Val Tyr
             20                  25                  30 tac tat agg aaa aat tta acc tgc act tgg agt cca gga aag gaa acc    144
Tyr Tyr Arg Lys Asn Leu Thr Cys Thr Trp Ser Pro Gly Lys Glu Thr
         35                  40                  45 agt tat acc cag tac aca gtt aag aga act tac gct ttt gga gaa aaa    192
Ser Tyr Thr Gln Tyr Thr Val Lys Arg Thr Tyr Ala Phe Gly Glu Lys
     50                  55                  60 cat gat aat tgt aca acc aat agt tct aca agt gaa aat cgt gct tcg    240
His Asp Asn Cys Thr Thr Asn Ser Ser Thr Ser Glu Asn Arg Ala Ser
 65                  70                  75                  80 tgc tct ttt ttc ctt cca aga ata acg atc cca gat aat tat acc att    288
Cys Ser Phe Phe Leu Pro Arg Ile Thr Ile Pro Asp Asn Tyr Thr Ile
                 85                  90                  95 gag gtg gaa gct gaa aat gga gat ggt gta att aaa tct cat atg aca    336
Glu Val Glu Ala Glu Asn Gly Asp Gly Val Ile Lys Ser His Met Thr
            100                 105                 110 tac tgg aga tta gag aac ata gcg aaa act gaa cca cct aag att ttc    384
Tyr Trp Arg Leu Glu Asn Ile Ala Lys Thr Glu Pro Pro Lys Ile Phe
        115                 120                 125 cgt gtg aaa cca gtt ttg ggc atc aaa cga atg att caa att gaa tgg    432
Arg Val Lys Pro Val Leu Gly Ile Lys Arg Met Ile Gln Ile Glu Trp
    130                 135                 140 ata aag cct gag ttg gcg cct gtt tca tct gat tta aaa tac aca ctt    480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct    528
Arg Phe Arg Thr Val Asn Ser Thr Ser Trp Met Glu Val Asn Phe Ala
                165                 170                 175 aag aac cgt aag gat aaa aac caa acg tac aac ctc acg ggg ctg cag    576
Lys Asn Arg Lys Asp Lys Asn Gln Thr Tyr Asn Leu Thr Gly Leu Gln
            180                 185                 190 cct ttt aca gaa tat gtc ata gct ctg cga tgt gcg gtc aag gag tca    624
Pro Phe Thr Glu Tyr Val Ile Ala Leu Arg Cys Ala Val Lys Glu Ser
        195                 200                 205 aag ttc tgg agt gac tgg agc caa gaa aaa atg gga atg act gag gaa    672
Lys Phe Trp Ser Asp Trp Ser Gln Glu Lys Met Gly Met Thr Glu Glu
    210                 215                 220
```

```
gaa ggc aag cta ctc cct gcg att ccc gtc ctg tct gct ctg gtg tag     720
Glu Gly Lys Leu Leu Pro Ala Ile Pro Val Leu Ser Ala Leu Val *
225                 230                 235
```

<210> SEQ ID NO 12
<211> LENGTH: 239
<212> TYPE: PRT
<213> ORGANISM: Homo sapiens

<400> SEQUENCE: 12

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Gly Lys Leu Leu Pro Ala Ile Pro Val Leu Ser Ala Leu Val
225                 230                 235
```

<210> SEQ ID NO 13
<211> LENGTH: 1989
<212> TYPE: DNA
<213> ORGANISM: Mus musculus
<220> FEATURE:
<221> NAME/KEY: CDS
<222> LOCATION: (1)...(1989)
<220> FEATURE:
<221> NAME/KEY: misc_feature
<222> LOCATION: (1)...(1989)
<223> OTHER INFORMATION: mouse IL-31RA

<400> SEQUENCE: 13

```
atg ctg agc agc cag aag gga tcc tgc agc cag gaa cca ggg gca gcc     48
Met Leu Ser Ser Gln Lys Gly Ser Cys Ser Gln Glu Pro Gly Ala Ala
1               5                   10                  15 cac gtc cag cct ctg ggt gtg aac gct gga ata atg tgg acc ttg gca     96
His Val Gln Pro Leu Gly Val Asn Ala Gly Ile Met Trp Thr Leu Ala
            20                  25                  30
```

```
ctg tgg gca ttc tct ttc ctc tgc aaa ttc agc ctg gca gtc ctg ccg    144
Leu Trp Ala Phe Ser Phe Leu Cys Lys Phe Ser Leu Ala Val Leu Pro
         35                  40                  45 act aag cca gag aac att tcc tgc gtc ttt tac ttc gac aga aat ctg    192
Thr Lys Pro Glu Asn Ile Ser Cys Val Phe Tyr Phe Asp Arg Asn Leu
 50                  55                  60 act tgc act tgg aga cca gag aag gaa acc aat gat acc agc tac att    240
Thr Cys Thr Trp Arg Pro Glu Lys Glu Thr Asn Asp Thr Ser Tyr Ile
 65                  70                  75                  80 gtg act ttg act tac tcc tat gga aaa agc aat tat agt gac aat gct    288
Val Thr Leu Thr Tyr Ser Tyr Gly Lys Ser Asn Tyr Ser Asp Asn Ala
                 85                  90                  95 aca gag gct tca tat tct ttt ccc cgt tcc tgt gca atg ccc cca gac    336
Thr Glu Ala Ser Tyr Ser Phe Pro Arg Ser Cys Ala Met Pro Pro Asp
            100                 105                 110 atc tgc agt gtt gaa gta caa gct caa aat gga gat ggt aaa gtt aaa    384
Ile Cys Ser Val Glu Val Gln Ala Gln Asn Gly Asp Gly Lys Val Lys
        115                 120                 125 tct gac atc aca tat tgg cat tta atc tcc ata gca aaa acc gaa cca    432
Ser Asp Ile Thr Tyr Trp His Leu Ile Ser Ile Ala Lys Thr Glu Pro
130                 135                 140 cct ata att tta agt gtg aat cca att tgt aat aga atg ttc cag ata    480
Pro Ile Ile Leu Ser Val Asn Pro Ile Cys Asn Arg Met Phe Gln Ile
145                 150                 155                 160 caa tgg aaa ccg cgt gaa aag act cgt ggg ttt cct tta gta tgc atg    528
Gln Trp Lys Pro Arg Glu Lys Thr Arg Gly Phe Pro Leu Val Cys Met
                165                 170                 175 ctt cgg ttc aga act gtc aac agt agc cgc tgg acg gaa gtc aat ttt    576
Leu Arg Phe Arg Thr Val Asn Ser Ser Arg Trp Thr Glu Val Asn Phe
            180                 185                 190 gaa aac tgt aaa cag gtc tgc aac ctc aca gga ctt cag gct ttc aca    624
Glu Asn Cys Lys Gln Val Cys Asn Leu Thr Gly Leu Gln Ala Phe Thr
        195                 200                 205 gaa tat gtc ctg gct cta cga ttc agg ttc aat gac tca aga tat tgg    672
Glu Tyr Val Leu Ala Leu Arg Phe Arg Phe Asn Asp Ser Arg Tyr Trp
    210                 215                 220 agc aag tgg agc aaa gaa gaa acc aga gtg act atg gag gaa gtt cca    720
Ser Lys Trp Ser Lys Glu Glu Thr Arg Val Thr Met Glu Glu Val Pro
225                 230                 235                 240 cat gtc ctg gac ctg tgg aga att ctg gaa cca gca gac atg aac gga    768
His Val Leu Asp Leu Trp Arg Ile Leu Glu Pro Ala Asp Met Asn Gly
                245                 250                 255 gac agg aag gtg cga ttg ctg tgg aag aag gca aga gga gcc ccc gtc    816
Asp Arg Lys Val Arg Leu Leu Trp Lys Lys Ala Arg Gly Ala Pro Val
            260                 265                 270 ttg gag aaa aca ttt ggc tac cac ata cag tac ttt gca gag aac agc    864
Leu Glu Lys Thr Phe Gly Tyr His Ile Gln Tyr Phe Ala Glu Asn Ser
        275                 280                 285 act aac ctc aca gag ata aac aac atc acc acc cag cag tat gaa ctg    912
Thr Asn Leu Thr Glu Ile Asn Asn Ile Thr Thr Gln Gln Tyr Glu Leu
    290                 295                 300 ctt ctg atg agc cag gca cac tct gtg tcc gtg act tct ttt aat tct    960
Leu Leu Met Ser Gln Ala His Ser Val Ser Val Thr Ser Phe Asn Ser
305                 310                 315                 320 ctt ggc aag tcc caa gag acc atc ctg agg atc cca gat gtc cat gag    1008
Leu Gly Lys Ser Gln Glu Thr Ile Leu Arg Ile Pro Asp Val His Glu
                325                 330                 335 aag acc ttc cag tac att aag agc atg cag gcc tac ata gcc gag ccc    1056
Lys Thr Phe Gln Tyr Ile Lys Ser Met Gln Ala Tyr Ile Ala Glu Pro
```

```
                340             345             350
ctg ttg gtg gtg aac tgg caa agc tcc att cct gcg gtg gac act tgg       1104
Leu Leu Val Val Asn Trp Gln Ser Ser Ile Pro Ala Val Asp Thr Trp
            355             360             365 ata gtg gag tgg ctc cca gaa gct gcc atg tcg aag ttc cct gcc ctt       1152
Ile Val Glu Trp Leu Pro Glu Ala Ala Met Ser Lys Phe Pro Ala Leu
    370             375             380 tcc tgg gaa tct gtg tct cag gtc acg aac tgg acc atc gag caa gat       1200
Ser Trp Glu Ser Val Ser Gln Val Thr Asn Trp Thr Ile Glu Gln Asp
385             390             395             400 aaa cta aaa cct ttc aca tgc tat aat ata tca gtg tat cca gtg ttg       1248
Lys Leu Lys Pro Phe Thr Cys Tyr Asn Ile Ser Val Tyr Pro Val Leu
            405             410             415 gga cac cga gtt gga gag ccg tat tca atc caa gct tat gcc aaa gaa       1296
Gly His Arg Val Gly Glu Pro Tyr Ser Ile Gln Ala Tyr Ala Lys Glu
        420             425             430 gga act cca tta aaa ggt cct gag acc agg gtg gag aac atc ggt ctg       1344
Gly Thr Pro Leu Lys Gly Pro Glu Thr Arg Val Glu Asn Ile Gly Leu
            435             440             445 agg aca gcc acg atc aca tgg aag gag att cct aag agt gct agg aat       1392
Arg Thr Ala Thr Ile Thr Trp Lys Glu Ile Pro Lys Ser Ala Arg Asn
450             455             460 gga ttt atc aac aat tac act gta ttt tac caa gct gaa ggt gga aaa       1440
Gly Phe Ile Asn Asn Tyr Thr Val Phe Tyr Gln Ala Glu Gly Gly Lys
465             470             475             480 gaa ctc tcc aag act gtt aac tct cat gcc ctg cag tgt gac ctg gag       1488
Glu Leu Ser Lys Thr Val Asn Ser His Ala Leu Gln Cys Asp Leu Glu
            485             490             495 tct ctg aca cga agg acc tct tat act gtt tgg gtc atg gcc agc acc       1536
Ser Leu Thr Arg Arg Thr Ser Tyr Thr Val Trp Val Met Ala Ser Thr
        500             505             510 aga gct gga ggt acc aac ggg gtg aga ata aac ttc aag aca ttg tca       1584
Arg Ala Gly Gly Thr Asn Gly Val Arg Ile Asn Phe Lys Thr Leu Ser
            515             520             525 atc agt gtg ttt gaa att gtc ctt cta aca tct cta gtt gga gga ggc       1632
Ile Ser Val Phe Glu Ile Val Leu Leu Thr Ser Leu Val Gly Gly Gly
        530             535             540 ctt ctt cta ctt agc atc aaa aca gtg act ttt ggc ctc aga aag cca       1680
Leu Leu Leu Leu Ser Ile Lys Thr Val Thr Phe Gly Leu Arg Lys Pro
545             550             555             560 aac cgg ttg act ccc ctg tgt tgt cct gat gtt ccc aac cct gct gaa       1728
Asn Arg Leu Thr Pro Leu Cys Cys Pro Asp Val Pro Asn Pro Ala Glu
            565             570             575 agt agt tta gcc aca tgg ctc gga gat ggt ttc aag aag tca aat atg       1776
Ser Ser Leu Ala Thr Trp Leu Gly Asp Gly Phe Lys Lys Ser Asn Met
        580             585             590 aag gag act gga aac tct ggg aac aca gaa gac gtg gtc cta aaa cca       1824
Lys Glu Thr Gly Asn Ser Gly Asn Thr Glu Asp Val Val Leu Lys Pro
            595             600             605 tgt ccc gtc ccc gcg gat ctc att gac aag ctg gta gtg aac ttt gag       1872
Cys Pro Val Pro Ala Asp Leu Ile Asp Lys Leu Val Val Asn Phe Glu
610             615             620 aat ttt ctg gaa gta gtt ttg aca gag gaa gct gga aag ggt cag gcg       1920
Asn Phe Leu Glu Val Val Leu Thr Glu Glu Ala Gly Lys Gly Gln Ala
625             630             635             640 agc att ttg gga gga gaa gcg aat gag tat atc tta tcc cag gaa cca       1968
Ser Ile Leu Gly Gly Glu Ala Asn Glu Tyr Ile Leu Ser Gln Glu Pro
            645             650             655 agc tgt cct ggc cat tgc tga                                            1989
```

Ser Cys Pro Gly His Cys *
           660

<210> SEQ ID NO 14
<211> LENGTH: 662
<212> TYPE: PRT
<213> ORGANISM: Mus musculus

<400> SEQUENCE: 14

Met Leu Ser Ser Gln Lys Gly Ser Cys Ser Gln Glu Pro Gly Ala Ala
1               5                   10                  15

His Val Gln Pro Leu Gly Val Asn Ala Gly Ile Met Trp Thr Leu Ala
            20                  25                  30

Leu Trp Ala Phe Ser Phe Leu Cys Lys Phe Ser Leu Ala Val Leu Pro
        35                  40                  45

Thr Lys Pro Glu Asn Ile Ser Cys Val Phe Tyr Phe Asp Arg Asn Leu
    50                  55                  60

Thr Cys Thr Trp Arg Pro Glu Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
    275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
    355                 360                 365

```
Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
            435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
            515                 520                 525

Ile Ser Val Phe Glu Ile Val Leu Leu Thr Ser Leu Val Gly Gly Gly
    530                 535                 540

Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
                565                 570                 575

Ser Ser Leu Ala Thr Trp Leu Gly Asp Gly Phe Lys Lys Ser Asn Met
            580                 585                 590

Lys Glu Thr Gly Asn Ser Gly Asn Thr Glu Asp Val Val Leu Lys Pro
            595                 600                 605

Cys Pro Val Pro Ala Asp Leu Ile Asp Lys Leu Val Val Asn Phe Glu
    610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
                645                 650                 655

Ser Cys Pro Gly His Cys
            660

<210> SEQ ID NO 15
<211> LENGTH: 2940
<212> TYPE: DNA
<213> ORGANISM: Homo sapiens
<220> FEATURE:
<221> NAME/KEY: CDS
<222> LOCATION: (1)...(2940)
<220> FEATURE:
<221> NAME/KEY: misc_feature
<222> LOCATION: (1)...(2940)
<223> OTHER INFORMATION: human OSMRbeta receptor

<400> SEQUENCE: 15 atg gct cta ttt gca gtc ttt cag aca aca ttc ttc tta aca ttg ctg      48
Met Ala Leu Phe Ala Val Phe Gln Thr Thr Phe Phe Leu Thr Leu Leu
  1               5                  10                  15 tcc ttg agg act tac cag agt gaa gtc ttg gct gaa cgt tta cca ttg      96
Ser Leu Arg Thr Tyr Gln Ser Glu Val Leu Ala Glu Arg Leu Pro Leu
```

|     |     |     |     |     |     |     |     |     |     |     |     |     |     |     |     |     |
|---|---|---|---|---|---|---|---|---|---|---|---|---|---|---|---|---|
|     |     |     | 20  |     |     |     | 25  |     |     |     | 30  |     |     |     |     |     |
| act | cct | gta | tca | ctt | aaa | gtt | tcc | acc | aat | tct | acg | cgt | cag | agt | ttg | 144 |
| Thr | Pro | Val | Ser | Leu | Lys | Val | Ser | Thr | Asn | Ser | Thr | Arg | Gln | Ser | Leu |     |
|     |     | 35  |     |     |     | 40  |     |     |     | 45  |     |     |     |     |     |     |
| cac | tta | caa | tgg | act | gtc | cac | aac | ctt | cct | tat | cat | cag | gaa | ttg | aaa | 192 |
| His | Leu | Gln | Trp | Thr | Val | His | Asn | Leu | Pro | Tyr | His | Gln | Glu | Leu | Lys |     |
|     | 50  |     |     |     | 55  |     |     |     | 60  |     |     |     |     |     |     |     |
| atg | gta | ttt | cag | atc | cag | atc | agt | agg | att | gaa | aca | tcc | aat | gtc | atc | 240 |
| Met | Val | Phe | Gln | Ile | Gln | Ile | Ser | Arg | Ile | Glu | Thr | Ser | Asn | Val | Ile |     |
| 65  |     |     |     |     | 70  |     |     |     |     | 75  |     |     |     |     | 80  |     |
| tgg | gtg | ggg | aat | tac | agc | acc | act | gtg | aag | tgg | aac | cag | gtt | ctg | cat | 288 |
| Trp | Val | Gly | Asn | Tyr | Ser | Thr | Thr | Val | Lys | Trp | Asn | Gln | Val | Leu | His |     |
|     |     |     |     |     | 85  |     |     |     |     | 90  |     |     |     |     | 95  |     |
| tgg | agc | tgg | gaa | tct | gag | ctc | cct | ttg | gaa | tgt | gcc | aca | cac | ttt | gta | 336 |
| Trp | Ser | Trp | Glu | Ser | Glu | Leu | Pro | Leu | Glu | Cys | Ala | Thr | His | Phe | Val |     |
|     |     |     |     | 100 |     |     |     |     | 105 |     |     |     |     | 110 |     |     |
| aga | ata | aag | agt | ttg | gtg | gac | gat | gcc | aag | ttc | cct | gag | cca | aat | ttc | 384 |
| Arg | Ile | Lys | Ser | Leu | Val | Asp | Asp | Ala | Lys | Phe | Pro | Glu | Pro | Asn | Phe |     |
|     |     |     | 115 |     |     |     |     | 120 |     |     |     |     | 125 |     |     |     |
| tgg | agc | aac | tgg | agt | tcc | tgg | gag | gaa | gtc | agt | gta | caa | gat | tct | act | 432 |
| Trp | Ser | Asn | Trp | Ser | Ser | Trp | Glu | Glu | Val | Ser | Val | Gln | Asp | Ser | Thr |     |
|     | 130 |     |     |     |     | 135 |     |     |     |     | 140 |     |     |     |     |     |
| gga | cag | gat | ata | ttg | ttc | gtt | ttc | cct | aaa | gat | aag | ctg | gtg | gaa | gaa | 480 |
| Gly | Gln | Asp | Ile | Leu | Phe | Val | Phe | Pro | Lys | Asp | Lys | Leu | Val | Glu | Glu |     |
| 145 |     |     |     |     | 150 |     |     |     |     | 155 |     |     |     |     | 160 |     |
| ggc | acc | aat | gtt | acc | att | tgt | tac | gtt | tct | agg | aac | att | caa | aat | aat | 528 |
| Gly | Thr | Asn | Val | Thr | Ile | Cys | Tyr | Val | Ser | Arg | Asn | Ile | Gln | Asn | Asn |     |
|     |     |     |     |     | 165 |     |     |     |     | 170 |     |     |     |     | 175 |     |
| gta | tcc | tgt | tat | ttg | gaa | ggg | aaa | cag | att | cat | gga | gaa | caa | ctt | gat | 576 |
| Val | Ser | Cys | Tyr | Leu | Glu | Gly | Lys | Gln | Ile | His | Gly | Glu | Gln | Leu | Asp |     |
|     |     |     | 180 |     |     |     |     | 185 |     |     |     |     | 190 |     |     |     |
| cca | cat | gta | act | gca | ttc | aac | ttg | aat | agt | gtg | cct | ttc | att | agg | aat | 624 |
| Pro | His | Val | Thr | Ala | Phe | Asn | Leu | Asn | Ser | Val | Pro | Phe | Ile | Arg | Asn |     |
|     |     | 195 |     |     |     |     | 200 |     |     |     |     | 205 |     |     |     |     |
| aaa | ggg | aca | aat | atc | tat | tgt | gag | gca | agt | caa | gga | aat | gtc | agt | gaa | 672 |
| Lys | Gly | Thr | Asn | Ile | Tyr | Cys | Glu | Ala | Ser | Gln | Gly | Asn | Val | Ser | Glu |     |
|     | 210 |     |     |     |     | 215 |     |     |     |     | 220 |     |     |     |     |     |
| ggc | atg | aaa | ggc | atc | gtt | ctt | ttt | gtc | tca | aaa | gta | ctt | gag | gag | ccc | 720 |
| Gly | Met | Lys | Gly | Ile | Val | Leu | Phe | Val | Ser | Lys | Val | Leu | Glu | Glu | Pro |     |
| 225 |     |     |     |     | 230 |     |     |     |     | 235 |     |     |     |     | 240 |     |
| aag | gac | ttt | tct | tgt | gaa | acc | gag | gac | ttc | aag | act | ttg | cac | tgt | act | 768 |
| Lys | Asp | Phe | Ser | Cys | Glu | Thr | Glu | Asp | Phe | Lys | Thr | Leu | His | Cys | Thr |     |
|     |     |     |     | 245 |     |     |     |     | 250 |     |     |     |     | 255 |     |     |
| tgg | gat | cct | ggg | acg | gac | act | gcc | ttg | ggg | tgg | tct | aaa | caa | cct | tcc | 816 |
| Trp | Asp | Pro | Gly | Thr | Asp | Thr | Ala | Leu | Gly | Trp | Ser | Lys | Gln | Pro | Ser |     |
|     |     |     | 260 |     |     |     |     | 265 |     |     |     |     | 270 |     |     |     |
| caa | agc | tac | act | tta | ttt | gaa | tca | ttt | tct | ggg | gaa | aag | aaa | ctt | tgt | 864 |
| Gln | Ser | Tyr | Thr | Leu | Phe | Glu | Ser | Phe | Ser | Gly | Glu | Lys | Lys | Leu | Cys |     |
|     |     | 275 |     |     |     |     | 280 |     |     |     |     | 285 |     |     |     |     |
| aca | cac | aaa | aac | tgg | tgt | aat | tgg | caa | ata | act | caa | gac | tca | caa | gaa | 912 |
| Thr | His | Lys | Asn | Trp | Cys | Asn | Trp | Gln | Ile | Thr | Gln | Asp | Ser | Gln | Glu |     |
|     |     | 290 |     |     |     |     | 295 |     |     |     |     | 300 |     |     |     |     |
| acc | tat | aac | ttc | aca | ctc | ata | gct | gaa | aat | tac | tta | agg | aag | aga | agt | 960 |
| Thr | Tyr | Asn | Phe | Thr | Leu | Ile | Ala | Glu | Asn | Tyr | Leu | Arg | Lys | Arg | Ser |     |
| 305 |     |     |     |     | 310 |     |     |     |     | 315 |     |     |     |     | 320 |     |
| gtc | aat | atc | ctt | ttt | aac | ctg | act | cat | cga | gtt | tat | tta | atg | aat | cct | 1008 |
| Val | Asn | Ile | Leu | Phe | Asn | Leu | Thr | His | Arg | Val | Tyr | Leu | Met | Asn | Pro |     |
|     |     |     |     |     | 325 |     |     |     |     | 330 |     |     |     |     | 335 |     |
| ttt | agt | gtc | aac | ttt | gaa | aat | gta | aat | gcc | aca | aat | gcc | atc | atg | acc | 1056 |

```
Phe Ser Val Asn Phe Glu Asn Val Asn Ala Thr Asn Ala Ile Met Thr
            340                 345                 350 tgg aag gtg cac tcc ata agg aat aat ttc aca tat ttg tgt cag att     1104
Trp Lys Val His Ser Ile Arg Asn Asn Phe Thr Tyr Leu Cys Gln Ile
            355                 360                 365 gaa ctc cat ggt gaa gga aaa atg atg caa tac aat gtt tcc atc aag     1152
Glu Leu His Gly Glu Gly Lys Met Met Gln Tyr Asn Val Ser Ile Lys
        370                 375                 380 gtg aac ggt gag tac ttc tta agt gaa ctg gaa cct gcc aca gag tac     1200
Val Asn Gly Glu Tyr Phe Leu Ser Glu Leu Glu Pro Ala Thr Glu Tyr
385                 390                 395                 400 atg gcg cga gta cgg tgt gct gat gcc agc cac ttc tgg aaa tgg agt     1248
Met Ala Arg Val Arg Cys Ala Asp Ala Ser His Phe Trp Lys Trp Ser
                405                 410                 415 gaa tgg agt ggt cag aac ttc acc aca ctt gaa gct gct ccc tca gag     1296
Glu Trp Ser Gly Gln Asn Phe Thr Thr Leu Glu Ala Ala Pro Ser Glu
            420                 425                 430 gcc cct gat gtc tgg aga att gtg agc ttg gag cca gga aat cat act     1344
Ala Pro Asp Val Trp Arg Ile Val Ser Leu Glu Pro Gly Asn His Thr
        435                 440                 445 gtg acc tta ttc tgg aag cca tta tca aaa ctg cat gcc aat gga aag     1392
Val Thr Leu Phe Trp Lys Pro Leu Ser Lys Leu His Ala Asn Gly Lys
    450                 455                 460 atc ctg ttc tat aat gta gtt gta gaa aac cta gac aaa cca tcc agt     1440
Ile Leu Phe Tyr Asn Val Val Val Glu Asn Leu Asp Lys Pro Ser Ser
465                 470                 475                 480 tca gag ctc cat tcc att cca gca cca gcc aac agc aca aaa cta atc     1488
Ser Glu Leu His Ser Ile Pro Ala Pro Ala Asn Ser Thr Lys Leu Ile
                485                 490                 495 ctt gac agg tgt tcc tac caa atc tgc gtc ata gcc aac aac agt gtg     1536
Leu Asp Arg Cys Ser Tyr Gln Ile Cys Val Ile Ala Asn Asn Ser Val
            500                 505                 510 ggt gct tct cct gct tct gta ata gtc atc tct gca gac ccc gaa aac     1584
Gly Ala Ser Pro Ala Ser Val Ile Val Ile Ser Ala Asp Pro Glu Asn
        515                 520                 525 aaa gag gtt gag gaa gaa aga att gca ggc aca gag ggt gga ttc tct     1632
Lys Glu Val Glu Glu Glu Arg Ile Ala Gly Thr Glu Gly Gly Phe Ser
    530                 535                 540 ctg tct tgg aaa ccc caa cct gga gat gtt ata ggc tat gtt gtg gac     1680
Leu Ser Trp Lys Pro Gln Pro Gly Asp Val Ile Gly Tyr Val Val Asp
545                 550                 555                 560 tgg tgt gac cat acc cag gat gtg ctc ggt gat ttc cag tgg aag aat     1728
Trp Cys Asp His Thr Gln Asp Val Leu Gly Asp Phe Gln Trp Lys Asn
                565                 570                 575 gta ggt ccc aat acc aca agc aca gtc att agc aca gat gct ttt agg     1776
Val Gly Pro Asn Thr Thr Ser Thr Val Ile Ser Thr Asp Ala Phe Arg
            580                 585                 590 cca gga gtt cga tat gac ttc aga att tat ggg tta tct aca aaa agg     1824
Pro Gly Val Arg Tyr Asp Phe Arg Ile Tyr Gly Leu Ser Thr Lys Arg
        595                 600                 605 att gct tgt tta tta gag aaa aaa aca gga tac tct cag gaa ctt gct     1872
Ile Ala Cys Leu Leu Glu Lys Lys Thr Gly Tyr Ser Gln Glu Leu Ala
    610                 615                 620 cct tca gac aac cct cac gtg ctg gtg gat aca ttg aca tcc cac tcc     1920
Pro Ser Asp Asn Pro His Val Leu Val Asp Thr Leu Thr Ser His Ser
625                 630                 635                 640 ttc act ctg agt tgg aaa gat tac tct act gaa tct caa cct ggt ttt     1968
Phe Thr Leu Ser Trp Lys Asp Tyr Ser Thr Glu Ser Gln Pro Gly Phe
                645                 650                 655
```

```
ata caa ggg tac cat gtc tat ctg aaa tcc aag gcg agg cag tgc cac    2016
Ile Gln Gly Tyr His Val Tyr Leu Lys Ser Lys Ala Arg Gln Cys His
            660                 665                 670 cca cga ttt gaa aag gca gtt ctt tca gat ggt tca gaa tgt tgc aaa    2064
Pro Arg Phe Glu Lys Ala Val Leu Ser Asp Gly Ser Glu Cys Cys Lys
        675                 680                 685 tac aaa att gac aac ccg gaa gaa aag gca ttg att gtg gac aac cta    2112
Tyr Lys Ile Asp Asn Pro Glu Glu Lys Ala Leu Ile Val Asp Asn Leu
    690                 695                 700 aag cca gaa tcc ttc tat gag ttt ttc atc act cca ttc act agt gct    2160
Lys Pro Glu Ser Phe Tyr Glu Phe Phe Ile Thr Pro Phe Thr Ser Ala
705                 710                 715                 720 ggt gaa ggc ccc agt gct acg ttc acg aag gtc acg act ccg gat gaa    2208
Gly Glu Gly Pro Ser Ala Thr Phe Thr Lys Val Thr Thr Pro Asp Glu
                725                 730                 735 cac tcc tcg atg ctg att cat atc cta ctg ccc atg gtt ttc tgc gtc    2256
His Ser Ser Met Leu Ile His Ile Leu Leu Pro Met Val Phe Cys Val
            740                 745                 750 ttg ctc atc atg gtc atg tgc tac ttg aaa agt cag tgg atc aag gag    2304
Leu Leu Ile Met Val Met Cys Tyr Leu Lys Ser Gln Trp Ile Lys Glu
        755                 760                 765 acc tgt tat cct gac atc cct gac cct tac aag agc agc atc ctg tca    2352
Thr Cys Tyr Pro Asp Ile Pro Asp Pro Tyr Lys Ser Ser Ile Leu Ser
    770                 775                 780 tta ata aaa ttc aag gag aac cct cac cta ata ata atg aat gtc agt    2400
Leu Ile Lys Phe Lys Glu Asn Pro His Leu Ile Ile Met Asn Val Ser
785                 790                 795                 800 gac tgt atc cca gat gct att gaa gtt gta agc aag cca gaa ggg aca    2448
Asp Cys Ile Pro Asp Ala Ile Glu Val Val Ser Lys Pro Glu Gly Thr
                805                 810                 815 aag ata cag ttc cta ggc act agg aag tca ctc aca gaa acc gag ttg    2496
Lys Ile Gln Phe Leu Gly Thr Arg Lys Ser Leu Thr Glu Thr Glu Leu
            820                 825                 830 act aag cct aac tac ctt tat ctc ctt cca aca gaa aag aat cac tct    2544
Thr Lys Pro Asn Tyr Leu Tyr Leu Leu Pro Thr Glu Lys Asn His Ser
        835                 840                 845 ggc cct ggc ccc tgc atc tgt ttt gag aac ttg acc tat aac cag gca    2592
Gly Pro Gly Pro Cys Ile Cys Phe Glu Asn Leu Thr Tyr Asn Gln Ala
    850                 855                 860 gct tct gac tct ggc tct tgt ggc cat gtt cca gta tcc cca aaa gcc    2640
Ala Ser Asp Ser Gly Ser Cys Gly His Val Pro Val Ser Pro Lys Ala
865                 870                 875                 880 cca agt atg ctg gga cta atg acc tca cct gaa aat gta cta aag gca    2688
Pro Ser Met Leu Gly Leu Met Thr Ser Pro Glu Asn Val Leu Lys Ala
                885                 890                 895 cta gaa aaa aac tac atg aac tcc ctg gga gaa atc cca gct gga gaa    2736
Leu Glu Lys Asn Tyr Met Asn Ser Leu Gly Glu Ile Pro Ala Gly Glu
            900                 905                 910 aca agt ttg aat tat gtg tcc cag ttg gct tca ccc atg ttt gga gac    2784
Thr Ser Leu Asn Tyr Val Ser Gln Leu Ala Ser Pro Met Phe Gly Asp
        915                 920                 925 aag gac agt ctc cca aca aac cca gta gag gca cca cac tgt tca gag    2832
Lys Asp Ser Leu Pro Thr Asn Pro Val Glu Ala Pro His Cys Ser Glu
    930                 935                 940 tat aaa atg caa atg gca gtc tcc ctg cgt ctt gcc ttg cct ccc ccg    2880
Tyr Lys Met Gln Met Ala Val Ser Leu Arg Leu Ala Leu Pro Pro Pro
945                 950                 955                 960 acc gag aat agc agc ctc tcc tca att acc ctt tta gat cca ggt gaa    2928
Thr Glu Asn Ser Ser Leu Ser Ser Ile Thr Leu Leu Asp Pro Gly Glu
                965                 970                 975
```

```
cac tac tgc taa                                                    2940
His Tyr Cys *

<210> SEQ ID NO 16
<211> LENGTH: 979
<212> TYPE: PRT
<213> ORGANISM: Homo sapiens

<400> SEQUENCE: 16

Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
```

```
                355                 360                 365
Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
        515                 520                 525

Lys Glu Val Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
            580                 585                 590

Pro Gly Val Arg Tyr Asp Phe Arg Ile Tyr Gly Leu Ser Thr Lys Arg
        595                 600                 605

Ile Ala Cys Leu Leu Glu Lys Lys Thr Gly Tyr Ser Gln Glu Leu Ala
    610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
            660                 665                 670

Pro Arg Phe Glu Lys Ala Val Leu Ser Asp Gly Ser Glu Cys Cys Lys
        675                 680                 685

Tyr Lys Ile Asp Asn Pro Glu Glu Lys Ala Leu Ile Val Asp Asn Leu
    690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser Met Leu Ile His Ile Leu Leu Pro Met Val Phe Cys Val
            740                 745                 750

Leu Leu Ile Met Val Met Cys Tyr Leu Lys Ser Gln Trp Ile Lys Glu
        755                 760                 765

Thr Cys Tyr Pro Asp Ile Pro Asp Pro Tyr Lys Ser Ser Ile Leu Ser
    770                 775                 780
```

```
Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
            805                 810                 815

Lys Ile Gln Phe Leu Gly Thr Arg Lys Ser Leu Thr Glu Thr Glu Leu
        820                 825                 830

Thr Lys Pro Asn Tyr Leu Tyr Leu Leu Pro Thr Glu Lys Asn His Ser
        835                 840                 845

Gly Pro Gly Pro Cys Ile Cys Phe Glu Asn Leu Thr Tyr Asn Gln Ala
    850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
            885                 890                 895

Leu Glu Lys Asn Tyr Met Asn Ser Leu Gly Glu Ile Pro Ala Gly Glu
        900                 905                 910

Thr Ser Leu Asn Tyr Val Ser Gln Leu Ala Ser Pro Met Phe Gly Asp
        915                 920                 925

Lys Asp Ser Leu Pro Thr Asn Pro Val Glu Ala Pro His Cys Ser Glu
    930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
            965                 970                 975

His Tyr Cys

<210> SEQ ID NO 17
<211> LENGTH: 5
<212> TYPE: PRT
<213> ORGANISM: Artificial Sequence
<220> FEATURE:
<223> OTHER INFORMATION: WSXWS peptide motif
<220> FEATURE:
<221> NAME/KEY: VARIANT
<222> LOCATION: (3)...(3)
<223> OTHER INFORMATION: Xaa = any amino acid

<400> SEQUENCE: 17

Trp Ser Xaa Trp Ser
1               5

<210> SEQ ID NO 18
<211> LENGTH: 12
<212> TYPE: DNA
<213> ORGANISM: Artificial Sequence
<220> FEATURE:
<223> OTHER INFORMATION: representative contig

<400> SEQUENCE: 18
atggcttagc tt                                                     12

<210> SEQ ID NO 19
<211> LENGTH: 12
<212> TYPE: DNA
<213> ORGANISM: Artificial Sequence
<220> FEATURE:
<223> OTHER INFORMATION: representative contig

<400> SEQUENCE: 19
tagcttgagt ct                                                     12
```

```
<210> SEQ ID NO 20
<211> LENGTH: 12
<212> TYPE: DNA
<213> ORGANISM: Artificial Sequence
<220> FEATURE:
<223> OTHER INFORMATION: representative contig

<400> SEQUENCE: 20
agccatcagc tg                                                         12
```

METHODS OF TREATING SKIN DISORDERS USING ANTI-IL-31RA ANTIBODIES

CROSS-REFERENCE TO RELATED APPLICATIONS

This application is a continuation of U.S. patent application Ser. No. 15/839,362, filed Dec. 12, 2017, now abandoned, which is a continuation of U.S. patent application Ser. No. 15/615,567, filed Jun. 6, 2017, now abandoned, which is a continuation of U.S. patent application Ser. No. 15/411,640, filed Jan. 20, 2017, now abandoned, which is a continuation of U.S. patent application Ser. No. 14/829,711, filed Aug. 19, 2015, now abandoned, which is a divisional of U.S. patent application Ser. No. 12/986,707, filed Jan. 7, 2011, now U.S. Pat. No. 9,139,651, which is a divisional of U.S. application Ser. No. 12/404,162, filed Mar. 13, 2009, now U.S. Pat. No. 7,871,618, which is a continuation of U.S. application Ser. No. 11/353,451, filed Feb. 14, 2006, abandoned, which claims the benefit of U.S. Patent Application Ser. No. 60/716,761, filed Sep. 13, 2005, U.S. Patent Application Ser. No. 60/694,867, filed Jun. 29, 2005, and U.S. Patent Application Ser. No. 60/653,283, filed Feb. 14, 2005, all of which are herein incorporated by reference.

BACKGROUND OF THE INVENTION

The skin plays an important role in the immune system and consists of layers. The epidermis is a surface layer. Underneath the epidermis is the dermis, a layer of connective tissue. Underneath the dermis, is the hypodermis, a layer of large amounts of adipose tissue. Circulating T lymphocytes migrate to the skin under normal and inflammatory conditions. The cutaneous lymphocyte antigen (CLA) is considered a homing receptor for T cells with tropism for the skin. Santamaria-Babi, L., *Eur. J. Dermatol.* 14:13-18, 2004. CLA is a carbohydrate structure which is expressed on memory T cells as an epitope of the single cell-surface protein named P-selectin glycoprotein ligand-1 (PSGL-1) and facilitates binding of T cells to E-selectin, an inducible adhesion molecule expressed on vascular endothelium. See Fuhlbrigge R C, et al., *Nature* 1997; 389:978-81.

Several diseases of the skin are known to express high levels of CLA+ T cells, including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. There is a need to treat such skin T cell mediated diseases.

The demonstrated in vivo activities of the cytokine family illustrate the enormous clinical potential of, and need for, other cytokines, cytokine agonists, and cytokine antagonists. The present invention addresses these needs by providing a method of treating such diseases with IL-31RA antagonists, e.g., IL-31RA soluble receptor or neutralizing IL-31RA monoclonal antibody or fragment, a receptor for the newly identified IL-31 cytokine. IL-31, when over-expressed in mice, results in dermatitis-like symptoms. Both skin-homing T cells and epidermal keratinocytes have been implicated in the pathology of skin diseases in humans The present invention provides such polypeptides for these and other uses that should be apparent to those skilled in the art from the teachings herein.

DETAILED DESCRIPTION OF THE INVENTION

Definitions

Prior to setting forth the invention in detail, it may be helpful to the understanding thereof to define the following terms:

Unless otherwise specified, "a," "an," "the," and "at least one" are used interchangeably and mean one or more than one.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' (SEQ ID NO:18) are 5'-TAGCTTgagtct-3' (SEQ ID NO:19) and 3'-gtcgac-TACCGA-5' (SEQ ID NO:20).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides novel methods of using IL-31RA antagonists in detection, diagnosis, and treatment of diseases, in particular, diseases that have a high correlation of cutaneous lymphocyte antigen (CLA). The present invention is based in part upon the discovery that a previously identified cytokine, IL-31 is expressed by skin-homing T cells, but not gut-homing T cells.

IL-31 is a recently discovered protein having the structure of a four-helical-bundle cytokine. This cytokine was previously identified as IL-31 and is fully described in U.S. patent application Ser. No. 10/352,554, filed Jan. 21, 2003. See published U.S. Patent Application No. 2003-0224487, and PCT application WO 03/060090, all herein incorporated by reference. See also, Dillon, et al., Nature Immunol. 5:752-760, 2004. IL-31 is a ligand with high specificity for the receptor IL-31RA and at least one additional subunit comprising OncostatinM receptor beta (OSMRbeta). The native polynucleotide and polypeptide sequences for human IL-31 are shown in SEQ ID NOs:1 and 2, respectively. The native polynucleotide and polypeptide sequences for mouse IL-31 are shown in SEQ ID NOs:3 and 4, respectively.

As used herein the term, IL-31 also means and is interchangeably referred to as Zcytor17lig, and IL-31RA also means and is interchangeably referred to as Zcytor17, as used in U.S. patent publication number 20030224487 (herein incorporated by reference), as shown above. The heterodimeric receptor for IL-31 was also described in 20030224487 as comprising zcytor17 (HUGO name, IL-31RA) and with at least one additional subunit comprising OncostatinM receptor beta (OSMRbeta).

The native polynucleotide and polypeptide sequences for the "long" form of IL-31RA are shown in SEQ ID NOs:5 and 6, respectively. The native polynucleotide and polypeptide sequences for the "short" form of IL-31RA are shown in SEQ ID NOs:7 and 8, respectively. Additionally, truncated forms of IL-31RA polypeptide appear to be naturally expressed. Both forms encode soluble IL-31RA receptors. The "long" soluble IL-31RA polynucleotide and polypeptide sequences are shown in SEQ ID NOs:9 and 10, respectively. The "short" soluble IL-31RA polynucleotide and polypeptide sequences are shown in SEQ ID NOs:11 and 12, respectively. The native polynucleotide and polypeptide sequences for mouse IL-31RA are shown in SEQ ID NOs:13 and 14, respectively. The native polynucleotide and polypeptide sequences for human OSMRbeta are shown in SEQ ID NOs:15 and 16, respectively. See PCT applications WO 02/00721 and WO 04/003140, both of which are incorporated by reference.

The secretory signal sequence of IL-31 is comprised of amino acid residues 1 (Met) to 23 (Ala), and the mature polypeptide is comprised of amino acid residues 24 (Ser) to 164 (Thr) as shown in SEQ ID NO:2. Further N-terminal sequencing analysis of purified IL-31 from 293T cells showed an N-terminus at residue 27 (Leu) as shown in SEQ ID NO:2, with the mature polypeptide comprised of amino acid residues 27 (Leu) to 164 (Thr) as shown in SEQ ID NO:2.

Cytokine receptor subunits are characterized by a multidomain structure comprising an extracellular domain, a transmembrane domain that anchors the polypeptide in the cell membrane, and an intracellular domain. The extracellular domain may be a ligand-binding domain, and the intracellular domain may be an effector domain involved in signal transduction, although ligand-binding and effector functions may reside on separate subunits of a multimeric receptor. The domains and structural features of the IL-31RA polypeptides (zcytor17) are further described below.

Analysis of the IL-31RA polypeptide encoded by the DNA sequence of SEQ ID NO:5 revealed an open reading frame encoding 732 amino acids (SEQ ID NO:6) comprising a predicted secretory signal peptide of 19 amino acid residues (residue 1 (Met) to residue 19 (Ala) of SEQ ID NO:6), and a mature polypeptide of 713 amino acids (residue 20 (Ala) to residue 732 (Val) of SEQ ID NO:6). Analysis of the IL-31RA polypeptide encoded by the DNA sequence of SEQ ID NO:7 revealed an open reading frame encoding 662 amino acids (SEQ ID NO:8) comprising a predicted secretory signal peptide of 32 amino acid residues (residue 1 (Met) to residue 32 (Ala) of SEQ ID NO:8), and a mature polypeptide of 630 amino acids (residue 33 (Ala) to residue 662 (Ile) of SEQ ID NO:8). In addition to the WSXWS motif (SEQ ID NO:17) (corresponding to residues 211 to 215 of SEQ ID NO:6; and residues 224 to 228 of SEQ ID NO:8), the receptor comprises an extracellular domain (residues 20 (Ala) to 519 (Glu) of SEQ ID NO:6; residues 33 (Ala) to 532 (Glu) of SEQ ID NO:8) which includes a cytokine-binding domain of approximately 200 amino acid residues (residues 20 (Ala) to 227 (Pro) of SEQ ID NO:6; residues 33 (Ala) to 240 (Pro) of SEQ ID NO:8); a domain linker (residues 122 (Thr) to 125 (Pro) of SEQ ID NO:6; residues 135 (Thr) to 138 (Pro) of SEQ ID NO:8); a penultimate strand region (residues 194 (Phe) to 202 (Arg) of SEQ ID NO:6; residues 207 (Phe) to 215 (Arg) of SEQ ID NO:8); a fibronectin type III domain (residues 228 (Cys) to 519 (Glu) of SEQ ID NO:6; residues 241 (Cys) to 532 (Glu) of SEQ ID NO:8); a transmembrane domain (residues 520 (Ile) to 543 (Leu) of SEQ ID NO:6; residues 533 (Ile) to 556 (Leu) of SEQ ID NO:8); complete intracellular signaling domain (residues 544 (Lys) to 732 (Val) of SEQ ID NO:6; and residues 557 (Lys) to 662 (Ile) of SEQ ID NO:8) which contains a "Box I" signaling site (residues 554 (Trp) to 560 (Pro) of SEQ ID NO:6; residues 567 (Trp) to 573 (Pro) of SEQ ID NO:8), and a "Box II" signaling site (residues 617 (Gln) to 620 (Phe) of SEQ ID NO:6; residues 630 (Gln) to 633 (Phe) of SEQ ID NO:8). Those skilled in the art will recognize that these domain boundaries are approximate, and are based on alignments with known proteins and predictions of protein folding. In addition to these domains, conserved receptor features in the encoded receptor include (as shown in SEQ ID NO:6) a conserved Cys residue at position 30 (position 43 as shown in SEQ ID NO:8), CXW motif (wherein X is any amino acid) at positions 40-42 of SEQ ID NO:6 (positions 53-55 as shown in SEQ ID NO:8), Trp residue at position 170 of SEQ ID NO:6 (position 183 as shown in SEQ ID NO:8), and a conserved Arg residue at position 202 of SEQ ID NO:6 (position 215 as shown in SEQ ID NO:8). The corresponding polynucleotides encoding the IL-31RA polypeptide regions, domains, motifs, residues and sequences described above are as shown in SEQ ID NOs:5 and 7.

Moreover, truncated forms of the IL-31RA polypeptide appear to be naturally expressed. Both forms encode soluble zcytor17 receptors. A polynucleotide encoding a "long-form" of the soluble zcytor17 receptor, truncated within the fibronectin type III domain, is shown in SEQ ID NO:9 and the corresponding polypeptide is shown in SEQ ID NO:10. This truncated form encodes residues 1 (Met) through 324 (Lys) of SEQ ID NO:6, and thus comprises an intact signal sequence, WSXWS (SEQ ID NO:17) motif, linker, cytokine binding domain, penultimate strand, and conserved, Cys, CXW motif, Trp and Arg residues as described above. A polynucleotide encoding a "short-form" of the soluble IL-31RA receptor, truncated at the end of the cytokine binding domain is shown in SEQ ID NO:11 and the corresponding polypeptide is shown in SEQ ID NO:12. This truncated form encodes a 239 residue polypeptide that is identical to residues 1 (Met) through 225 (Glu) of SEQ ID NO:6 and then diverges, and thus comprises an intact signal sequence, WSXWS (SEQ ID NO:17) motif, linker, cytokine binding domain, penultimate strand, and conserved, Cys, CXW motif, Trp and Arg residues as described above.

Both skin-homing T cells and epidermal keratinocytes have been implicated in the pathology of skin diseases in humans. As shown herein, IL-31 mRNA and protein expression is restricted to the skin-homing CLA+ T cell population in both atopic dermatitis (AD) patients and normal individuals, while analysis of the receptor for IL-31, IL-31RA, by immunohistochemistry (IHC) suggests slightly higher levels of IL-31RA expression on skin keratinocytes in skin biopsies from acute and chronic AD sufferers compared to normal individuals.

When over-expressed in mice, IL-31 results in pruritus and the development of skin dermatitis resembling human atopic dermatitis (AD) Immunohistochemistry (IHC) studies shown herein show that IL-31RA protein was expressed by skin keratinocytes and infiltrating macrophages in skin biopsies from AD patients. Comparisons between AD patients and normal individuals suggested that IL-31RA was expressed at higher levels on epidermal keratinocytes in the AD samples. Skin cell infiltrates, which were present at greater numbers in skin of AD patients compared to normal individuals, expressed IL-31 mRNA. Histomorphometric analysis of these cells suggested a lymphocytic lineage with the majority of cells staining positive for cutaneous lymphocyte antigen (CLA) and CD3, demonstrating that skin-homing T cells in skin express IL-31 mRNA. Upon analysis of peripheral blood T cells for IL-31, IL-31 mRNA and protein expression is largely restricted to CD45RO+ CLA+ skin-homing T cells in AD and normal volunteers. Moreover, circulating CLA+ T cells from AD patients are capable of producing higher levels of IL-31 compared to CLA+ T cells from normal individuals, though there is large variability between patient samples. These results provide strong evidence that IL-31 expression is associated with atopic dermatitis and may contribute to the development of AD skin inflammation and pruritus.

As shown herein, IL-31 is produced both locally in the skin and by skin infiltrating cells. Local production of cytokines in tissues by T cells is thought to be a key mechanism for disease pathogenesis in AD and increased numbers of T cells both in circulation and in skin is thought to correlate with disease.

Although both AD patients and normal controls have circulating CLA+ T cells that express IL-31 upon activation, CLA+ T cells from AD patients are reported to exist in a more activated state compared to cells from normal individuals. See Akdis M, *J Immunol.*, 159:4611-4619, 1997. Consequently, the threshold of stimulation required for the production of IL-31 by CLA+ T cells may differ between dermatitis patients and control subjects. As shown herein, circulating CLA+ T cells from AD patients after 24 hours of stimulation with sub-optimal concentrations of anti-CD3 in the absence of anti-CD28 have the capacity to produce higher levels of IL-31 compared to cells from normal individuals. Due to the variability in IL-31 levels produced by CLA+ T cells from individual AD patients, there was no significant difference in the average IL-31 production from circulating CLA+ T cells of AD and normal individuals. Nevertheless, since more CLA+ T cells are localized in skin of AD patients, as compared to normal individuals, there is an increased potential for IL-31 activity in the AD skin micro-environment.

Example 1 demonstrates that circulating CLA+ T cells from some AD patients produce higher levels of IL-31 compared to cells from normal individuals. The detection of IL-31 in patients of such a subpopulation using the bioassay provided herein, or with any assay that detects IL-31 produced by circulating T cells in the blood, may be useful to determine if an IL-31 antagonist will be useful as treatment for diseases wherein the presence of IL-31 causes inflammation.

A cell line that is dependent on the OSMRbeta and IL-31RA linked pathway for survival and growth in the absence of other growth factors can be used to measure the activity of IL-31. Such growth factor-dependent cell lines include BaF3, FDC-P1, and MO7e. For information on the BaF3 cell line, see Palacios and Steinmetz, (*Cell*, 41:727-734, 1985) and Mathey-Prevot et al., (*Mol. Cell. Biol.*, 6:4133-4135, 1986). For information on the FDC-P1cell line, see Hapel et al. (*Blood*, 64:786-790, 1984). For information on the MO7e cell line, see Kiss et al., (*Leukemia*, 7:235-240, 1993).

The amino acid sequence for the OSMRbeta, and IL-31RA receptors indicated that the encoded receptors belonged to the Class I cytokine receptor subfamily that includes, but is not limited to, the receptors for IL-2, IL-4, IL-7, Lif, IL-12, IL-15, EPO, TPO, GM-CSF and G-CSF (for a review see, Cosman, "The Hematopoietin Receptor Superfamily" in *Cytokine* 5(2): 95-106, 1993). The IL-31RA receptor is fully described in PCT Patent Application No. US01/20484 (WIPO publication No. WO 02/00721). Analysis of the tissue distribution of the mRNA of the IL-31RA receptor revealed expression in activated CD4+ and CD8+ T-cell subsets, CD14+ monocytes, and weaker expression in CD19+ B-cells. Moreover, the mRNA was present in both resting or activated monocytic cell lines THP-1 (ATCC No. TIB-202), U937 (ATCC No. CRL-1593.2) and HL60 (ATCC No. CCL-240).

Antigenic epitope-bearing peptides and polypeptides preferably contain at least four to ten amino acids, at least ten to fourteen amino acids, or about fourteen to about thirty amino acids of the extracellular domains of SEQ ID NO:6 or SEQ ID NO:8. Such epitope-bearing peptides and polypeptides can be produced by fragmenting the extracellular domain of IL-31RA polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

The IL-31RA polypeptides of the present invention, including full-length polypeptides, functional fragments, and fusion polypeptides, can be produced, purified and refolded by methods well-known in the art and as described in PCT applications WO 02/00721 and WO 04/003140. It is preferred to purify the polypeptides of the present invention to ≥80% purity, more preferably to ≥90% purity, even more preferably 95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

The present invention provides methods for using IL-31RA antagonists, including anti-IL-31RA antibodies and fragments, soluble IL-31RA receptors, and soluble IL-31RA/OSMRbeta receptors for reducing, inhibiting, or preventing inflammation in cell microenvironments where one or more cells in the microenvironment is/are T cells that are positive for the cutaneous lymphocyte antigen.

Antibodies from an immune response generated by inoculation of an animal with IL-31RA antigens, e.g., extracellular domain of SEQ ID NO:6 or a portion thereof, such as ligand binding domain) can be isolated and purified are known in the art and are described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a IL-31RA polypeptide or a fragment thereof. The immunogenicity of an IL-31RA polypeptide may be increased through the use of an adjuvant, such as alum (aluminum hydroxide) or Freund's complete or incomplete adjuvant. Polypeptides useful for immunization also include fusion polypeptides, such as fusions of IL-31RA or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as Fab fragment, Fab' fragment, F(ab')$_2$ fragment, single chain Fv (scFv) proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication No. WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-IL-31RA antibodies herein bind to an IL-31RA polypeptide, peptide or epitope with an affinity at least 10-fold greater than the binding affinity to control (non-IL-31RA) polypeptide. It is preferred that the antibodies exhibit a binding affinity (Ka) of $10^6$ M−1 or greater, preferably $10^7$ M−1 or greater, more preferably 108 M−1 or greater, and most preferably $10^9$ M−1 or greater. The binding affinity of an antibody can be readily determined by one of ordinary skill in the art, for example, by Scatchard analysis (Scatchard, G., *Ann. NY Acad. Sci.* 51: 660-672, 1949).

The present invention provides a method of treating a patient suffering from a skin disorder, the method comprises administering a therapeutically effective amount of an anti-IL-31RA antibody or fragment to the patient, wherein the anti-IL-31RA antibody or fragment binds with amino acid residues 20-519 of SEQ ID NO:6 or portion thereof, or amino acid residues 33-532 of SEQ ID NO:8 or portion thereof, and wherein the anti-IL-31RA antibody or fragment prevents, inhibits the progression of, delays the onset of, reduces the severity of, and/or inhibits at least one of the conditions or symptoms of the skin disorder selected from the group consisting of Atopic Dermititis, Contact dermatitis, Drug induced delayed type cutaneous allergic reactions, Toxic epidermal necrolysis, Cutaneous T cell Lymphoma, Bullous pemphigoid, Alopecia aereata, Vitiligo, Acne Rosacea, Prurigo nodularis, Scleroderma, and Herpes simplex virus. The anti-IL-31RA antibody may optionally be a polyclonal antibody or a neutralizing monoclonal antibody (the present invention also provides for a hybridoma for producing the neutralizing IL-31RA monoclonal antibody). The anti-IL-31RA antibody fragment may optionally be a Fab fragment, a Fab' fragment, a F(ab')2 fragment, single chain Fv (scFV), dual specific antibody, domain antibody, or bispecific antibody. The anti-IL-31RA antibody or fragment may bind with amino acid residues 20-277 of SEQ ID NO:6 or 33-240 of SEQ ID NO:8. The anti-IL-31RA antibody or fragment may bind with about 4-10 amino acid residues of amino acid residues 20-519 of SEQ ID NO:6 or amino acid residues 33-532 of SEQ ID NO:8. The anti-IL-31RA antibody or fragment may bind with about 10-14 amino acid residues of amino acid residues 20-519 of SEQ ID NO:6 or amino acid residues 33-532 of SEQ ID NO:8. The anti-IL-31RA antibody or fragment may bind with about 14-30 amino acid residues of amino acid residues 20-519 of SEQ ID NO:6 or amino acid residues 33-532 of SEQ ID NO:8. The anti-IL-31 antibody or fragment may be further conjugated to a polyethylene glycol or to human serum albumin.

The present invention also provides for a method of treating a patient suffering from a skin disorder, the method comprises administering a therapeutically effective amount of a soluble IL-31RA receptor to the patient, wherein the soluble IL-31RA receptor binds with an IL-31 polypeptide consisting of amino acid residues 1-164 SEQ ID NO:2, and wherein the soluble IL-31RA receptor prevents, inhibits the progression of, delays the onset of, reduces the severity of, and/or inhibits at least one of the conditions or symptoms of the skin disorder selected from the group consisting of Atopic Dermititis, Contact dermatitis, Drug induced delayed type cutaneous allergic reactions, Toxic epidermal necrolysis, Cutaneous T cell Lymphoma, Bullous pemphigoid, Alopecia aereata, Vitiligo, Acne Rosacea, Prurigo nodularis, Scleroderma, and Herpes simplex virus. The soluble IL-31RA receptor may comprise amino acid residues 20-519 of SEQ ID NO:6 or 33-240 of SEQ ID NO:8, amino acid residues 1-324 of SEQ ID NO:10, or amino acid residues 1-239 of SEQ ID NO:12. The soluble IL-31RA receptor may be further conjugated to the Fc region of the various immunoglobulins (IgG, IgA, IgD, IgM or IgE). Optionally, the soluble IL-31RA receptor may be an IL-31RA homodimer or an IL-31RA/OSMRbeta heterodimer. The soluble IL-31RA receptor may bind with an IL-31 polypeptide comprising, consisting essentially of, consisting of amino acid residues 24-164 of SEQ ID NO:2 or 27-164 of SEQ ID NO:2. The soluble IL-31RA receptor may be further conjugated to a polyethylene glycol or to human serum albumin.

The present invention also provides isolated IL-31RA encoding nucleic acid molecules that can hybridize under stringent conditions to nucleic acid molecules having the nucleotide sequence of nucleotides 58-1557 of SEQ ID NO:5 or nucleotides 97-1596 SEQ ID NO:7, or to nucleic acid molecules having a nucleotide sequence complementary to nucleotides 58-1557 of SEQ ID NO:5 or to nucleotides 97-1596 SEQ ID NO:7. In general, stringent conditions are selected to be about 5*C lower than the thermal melting point (Tm) for the specific sequence at a defined ionic strength and pH. The Tm is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The Tm of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases.

It is well within the abilities of one skilled in the art to adapt these conditions for use with a particular polynucleotide hybrid. The Tm for a specific target sequence is the temperature (under defined conditions) at which 50% of the target sequence will hybridize to a perfectly matched probe sequence. Those conditions which influence the Tm include, the size and base pair content of the polynucleotide probe, the ionic strength of the hybridization solution, and the presence of destabilizing agents in the hybridization solution. Numerous equations for calculating Tm are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, Crit. Rev. Biochem. Mol. Biol. 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating Tm based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated Tm. For smaller probes, <50 base pairs, hybridization is typically carried out at the Tm or 5-10° C. below the calculated Tm. This allows for the maximum rate of hybridization for DNA-DNA and DNA-RNA hybrids.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant IL-31RA polypeptide hybridize with a nucleic acid molecule having the nucleotide sequence of nucleotides 58-1557 of SEQ ID NO:5 (or its complement) or nucleotides 97-1596 SEQ ID NO:7 (or its complement) under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant IL-31RA polypeptide hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated IL-31RA polypeptides that have a substantially similar sequence identity to the polypeptides having amino acid residues 20-519 of SEQ ID NO:6 and/or amino acid residues 33-532 of SEQ ID NO:8, or their orthologs. The term "substantially similar sequence identity" is used herein to denote polypeptides comprising at least 70%, at least 80%, at least 90%, at least 95%, at least 96%, at least 97%, at least 98%, at least 99%, at least 99-0.5%, or greater than 99.5% sequence identity to the sequences shown in amino acid residues 20-519 of SEQ ID NO:6 and/or amino acid residues 33-532 of SEQ ID NO:8, or their orthologs. The present invention further includes nucleic acid molecules that encode such polypeptides. Methods for determining percent identity are described PCT publications WO 02/00721 (incorporated by reference) and 04/003140 (incorporated by reference).

The present invention provides a method of treating a patient suffering from a skin disorder, the method comprises administering a therapeutically effective amount of an anti-IL-31RA antibody or fragment to the patient, wherein the anti-IL-31RA antibody or fragment binds with an amino acid sequence having at least 90%, at least 91%, at least 92%, at least 93%, at least 94%, at least 95%, at least 96%, at least 97%, at least 98%, at least 99%, at least 99.5%, or great than 99.5% sequence identity with amino acid residues 20-519 of SEQ ID NO:6 or portion thereof, or amino acid residues 33-532 of SEQ ID NO:8 or portion thereof, and wherein the anti-IL-31RA antibody or fragment prevents, inhibits the progression of, delays the onset of, reduces the severity of, and/or inhibits at least one of the conditions or symptoms of the skin disorder selected from the group consisting of Atopic Dermititis, Contact dermatitis, Drug induced delayed type cutaneous allergic reactions, Toxic epidermal necrolysis, Cutaneous T cell Lymphoma, Bullous pemphigoid, Alopecia aereata, Vitiligo, Acne Rosacea, Prurigo nodularis, Scleroderma, and Herpes simplex virus. The anti-IL-31RA antibody may optionally be a polyclonal antibody or a neutralizing monoclonal antibody (the present invention also provides for a hybridoma for producing the neutralizing IL-31RA monoclonal antibody). The anti-IL-31RA antibody fragment may optionally be a Fab fragment, a Fab' fragment, a F(ab')2 fragment, single chain Fv (scFV), dual specific antibody, domain antibody, or bispecific antibody. The anti-IL-31RA antibody or fragment may bind with amino acid residues 20-277 of SEQ ID NO:6 or 33-240 of SEQ ID NO:8. The anti-IL-31RA antibody or fragment may bind with about 4-10 amino acid residues of amino acid residues 20-519 of SEQ ID NO:6 or amino acid residues 33-532 of SEQ ID NO:8. The anti-IL-31RA antibody or fragment may bind with about 10-14 amino acid residues of amino acid residues 20-519 of SEQ ID NO:6 or amino acid residues 33-532 of SEQ ID NO:8. The anti-IL-31RA antibody or fragment may bind with about 14-30 amino acid residues of amino acid residues 20-519 of SEQ ID NO:6 or amino acid residues 33-532 of SEQ ID NO:8. The anti-IL-31 antibody or fragment may be further conjugated to a polyethylene glycol or to human serum albumin.

The present invention also provides for a method of treating a patient suffering from a skin disorder, the method comprises administering a therapeutically effective amount of a soluble IL-31RA receptor to the patient, wherein the soluble IL-31RA receptor has at least 90%, at least 91%, at least 92%, at least 93%, at least 94%, at least 95%, at least 96%, at least 97%, at least 98%, at least 99%, at least 99.5%, or great than 99.5% sequence identity with amino acid residues 20-519 of SEQ ID NO:6 or portion thereof, or amino acid residues 33-532 of SEQ ID NO:8, and wherein the soluble IL-31RA receptor binds with an IL-31 polypeptide consisting of amino acid residues 1-164 SEQ ID NO:2, and wherein the soluble IL-31RA receptor prevents, inhibits the progression of, delays the onset of, reduces the severity of, and/or inhibits at least one of the conditions or symptoms of the skin disorder selected from the group consisting of Atopic Dermititis, Contact dermatitis, Drug induced delayed type cutaneous allergic reactions, Toxic epidermal necrolysis, Cutaneous T cell Lymphoma, Bullous pemphigoid, Alopecia aereata, Vitiligo, Acne Rosacea, Prurigo nodularis, Scleroderma, and Herpes simplex virus. The soluble IL-31RA receptor may comprise amino acid residues 20-519 of SEQ ID NO:6 or 33-240 of SEQ ID NO:8, amino acid residues 1-324 of SEQ ID NO:10, or amino acid residues 1-239 of SEQ ID NO:12. The soluble IL-31RA receptor may be further conjugated to the Fc region of the various immunoglobulins (IgG, IgA, IgD, IgM or IgE). Optionally, the soluble IL-31RA receptor may be an IL-31RA homodimer or an IL-31RA/OSMRbeta heterodimer. The soluble IL-31RA receptor may bind with an IL-31 polypeptide comprising, consisting essentially of, consisting of amino acid residues 24-164 of SEQ ID NO:2 or 27-164 of SEQ ID NO:2. The soluble IL-31RA receptor may be further conjugated to a polyethylene glycol or to human serum albumin.

A variety of assays known to those skilled in the art can be utilized to detect antibodies which bind to IL-31RA proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant IL-31RA protein or polypeptide.

Antibodies to IL-31RA may be used for tagging cells that express IL-31RA; for isolating IL-31RA by affinity purification; for diagnostic assays for determining circulating levels of IL-31RA polypeptides; for detecting or quantitating soluble IL-31RA as a marker of underlying pathology or disease; in analytical methods employing FACS; for screening expression libraries; for generating anti-idiotypic antibodies; and as neutralizing antibodies or as antagonists to block IL-31 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. In addition, antibodies to IL-31RA or fragments thereof may be used in vitro to detect denatured IL-31RA or fragments thereof in assays, for example, Western Blots or other assays known in the art.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, *Pseudomonas exotoxin*, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting carrier or vehicle for cell/tissue-specific delivery of generic anti-complementary-detectable/cytotoxic molecule conjugates.

Both skin-homing T cells and epidermal keratinocytes have been implicated in the pathology of skin diseases in humans. As shown in Example 1 herein, of the T cell subsets, IL-31 mRNA and protein expression is restricted to the skin-homing CLA+ T cell population in humans. As such, an antagonist to IL-31RA, including an antibody or fragment thereof or soluble receptor (IL-31RA and IL-31RA/OSMRbeta soluble receptors) antagonist will be useful in treating, ablating, inhibiting the progression of, and/or reducing the severity of skin and epidermal diseases which have expression of CLA+T cells. Such diseases include, for example, atopic dermatitis, contact dermatitis, psoriasis, drug-induced allergic reactions, skin-tropic viruses and viral associated pruritus, vitiligo, cutaneous T cell lymphoma, alopecia aerata, acne rosacea, acne vulgaris, prurigo nodularis, and bullous pemphigoid.

Atopic Dermatitis

Atopic dermatitis (AD) is a chronically relapsing inflammatory skin disease with a dramatically increasing incidence over the last decades. Clinically AD is characterized by highly pruritic often excoriated plaques and papules that show a chronic relapsing course. The diagnosis of AD is mostly based on major and minor clinical findings. See Hanifin J M, *Arch Dermatol:* 135, 1551 (1999). Histopathology reveals spongiosis, hyper and focal parakeratosis in acute lesions, whereas marked epidermal hyperplasia with hyper and parakeratosis, acanthosis/hypergranulosis and perivascular infiltration of the dermis with lymphocytes and abundant mast cells are the hallmarks of chronic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol:* 14, 13, (2004)). A significant increase in circulating CLA+ T cells among AD patients compared with control individuals has been documented (See Teraki Y., et al., *Br J Dermatol:* 143, 373 (2000)), while others have demonstrated that memory CLA+ T cells from AD patients preferentially respond to allergen extract compared to the CLA− population (See Santamaria-Babi, L. F., et al., *J Exp Med:*181, 1935, (1995)). In humans, the pathogenesis of atopic disorders of the skin have been associated with increases in CLA+ T cells that express increased levels of Th-2-type cytokines like IL-5 and IL-13. See Akdis M., et al., *Eur J Immunol:* 30, 3533 (2000); and Hamid Q., et al., *J Allergy Clin Immunol:* 98, 225 (1996).

NC/Nga Mice spontaneously develop AD-like lesions that parallel human AD in many aspects, including clinical course and signs, histopathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy:* 58, 139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest,* 101: 1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Both the NC/Nga spontaneous AD model and the OVA epicutaneous DO11.10 model are used to investigate expression of IL-31 and IL-31RA in AD. See Example 3.

An IL-31RA neutralizing antagonist could be effective in inhibiting, reducing, minimizing or preventing atopic dermatitis reactions. See Example 3 for an in vivo model for testing the effect of an IL-31 antagonist in an atopic dermatitis model.

Contact Dermatitis

Allergic contact dermatitis is defined as a T cell mediated immune reaction to an antigen that comes into contact with the skin. The CLA+ T cell population is considered to be involved in the initiation of dermatitis since allergen dependent T cell responses are largely confined to the CLA+ population of cells (See Santamaria-Babi, L. F., et al., *J Exp Med:*181, 1935, (1995)). Recent data has found that only memory (CD45RO+) CD4+ CLA+ and not CD8+ T cells proliferate and produce both type-1 (IFN-γ) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol:*51, 32, (2004).

In animal models, it has been demonstrated that allergic contact dermatitis is T-cell dependent and that the allergic-responsive T cells migrate to the site of allergen application. See generally: Engeman T. M., et al., *J Immunol:* 164, 5207, (2000); Ferguson T. A. & Kupper T. S. *J Immunol:* 150, 1172, (1993); and Gorbachev A. V. & Fairchild R. L. *Crit Rev Immunol:* 21, 451(2001). Since CLA+ T cells produce IL-31 and IL-31 stimulation of skin keratinocytes can induce pro-inflammatory chemokines, IL-31 may be involved in the pathophysiology of contact dermatitis.

An IL-31RA neutralizing antagonist, e.g., antibody or fragment thereof or soluble receptor (IL-31RA and IL-31RA/OSMRbeta soluble receptors), could be effective in inhibiting, reducing, minimizing or preventing contact dermatitis reactions. See Example 2 for an in vivo model for testing the effect of an IL-31 antagonist in a contact dermatitis model.

Drug-Induced Delayed Type Cutaneous Allergic Reactions

Drug-induced delayed type cutaneous allergic reactions are very heterogeneous and may mirror many distinct pathophysiological events. See Brockow K., et al., *Allergy*, 57, 45 (2002). Immunological mechanisms involved in these reactions have been shown as either antibody or cell mediated. In immediate drug allergy an IgE-mediated antibody reaction can be demonstrated by a positive skin prick and/or intradermal test after 20 min, whereas non-immediate reactions to drugs can occur more than one hour after last drug intake and are often T-cell mediated. Non-immediate T-cell mediated delayed type reactions can occur in patients with adverse drug reactions to penicillins for example Proliferative T cell responses to penicillins have been shown to be restricted to the memory (CD45RO+) CLA+ subpopulation of T cells from penicillin allergic patients whereas the CD45RO+ CLA- subset shows no proliferative response. See Blanca M., Leyva L., et al., *Blood Cells Mol Dis:*31, 75 (2003). Delayed-type hypersensitivity (DTH) reactions can be artificially reproduced in mice, allowing assessment of factors that may be involved in the initiation and perpetuation of the DTH response. An IL-31RA neutralizing antagonist, e.g., antibody or soluble receptor (IL-31RA and IL-31RA/OSMRbeta soluble receptors), could be effective in inhibiting, reducing, minimizing or preventing delayed type hypersensitivity reactions. See Example 4 for an in vivo model of testing the effect of an IL-31 antagonist in a DTH model.

Toxic epidermal necrolysis (TEN) is a very rare but extremely severe drug reaction characterized by widespread apoptosis of epidermis with extensive blisters. Studies have shown that lymphocytes infiltrating the blister are CLA+ T cells and can exhibit cytotoxicity towards epidermal keratinocytes. See Leyva L., et al., *J Allergy Clin Immunol:* 105, 157 (2000); and Nassif A., Bensussan A., et al., *J Allergy Clin Immunol:*114, 1209 2004). A transgenic mouse system, whereby OVA is expressed under the control of the keratin-5 (K5) promoter in the epidermal and hair follicular keratinocytes of mice, has been generated to establish an animal model for TEN. OVA specific CD8+ T cells, when adoptively transferred into K5-OVA mice, undergo activation and proliferation in the skin-draining lymph nodes and target the skin of K5-OVA mice, resulting in development of skin lesions that are reminiscent of TEN. See Azukizawa H., et al., *Eur J Immunol:* 33, 1879 (2003). An IL-31RA neutralizing antagonist, e.g., antibody or soluble receptor (IL-31RA and IL-31RA/OSMRbeta soluble receptors), could be effective in inhibiting, reducing, minimizing or preventing TEN reactions.

Bullous Pemphigoid

Bullous pemphigoid is a subepidermal disorder which manifests as subepidermal blisters with a dermal infiltrate of neutrophils and eosinophils. Diagnosis is characterized by the presence of antigen-specific antibodies against specific adhesion proteins of the epidermis and dermal-epidermal junction. See Jordon R. E., et al., *JAMA:* 200, 751 (1967). Studies analyzing the role of T cells in the pathogenesis of bullous pemphigoid by analysis of PBL and skin blister T cells have found a predominance of CLA+ T cells expressing increased levels of Th2-cytokines like IL-4 and IL-13. See Teraki Y., et al., *J Invest Dermatol:* 117, 1097 (2001). In bullous pemphigoid patients following therapy with systemic corticosteroids, the frequency of CLA+, but not CLA-, interleukin-13-producing cells is significantly decreased. Decreases in CLA+ cells following corticosteroid treatment is associated with clinical improvement. See Teraki, ibid. Neutralization of IL-31 by an IL-31RA antagonist, e.g., antibody or fragment thereof or soluble receptor (IL-31RA and IL-31RA/OSMRbeta soluble receptors), may improve clinical outcome of bullous pemohigoid.

Alopecia Areata

Alopecia areata (AA) is regarded as a tissue-restricted autoimmune disease of hair follicles in which follicular activity is arrested because of the continued activity of lymphocytic infiltrates. AA results in patches of complete hair loss anywhere on the body, though actual loss of hair follicles does not occur, even in hairless lesions. Although clinical signs of inflammation are absent, skin biopsies from sites of active disease show perifollicular lymphocytic inflammation of primarily CD4+ cells, along with a CD8+ intrafollicular infiltrate. See Kalish R. S. & Gilhar A. *J Investig Dermatol Symp Proc:* 8, 164 (2003).

Studies have shown that scalp skin infiltrating CD4+ or CD8+ lymphocytes express CLA and, in peripheral blood of individuals with AA, the percent of CLA+ CD4+ or CD8+ lymphocytes is significantly higher than that of normal controls. Furthermore, patients with severe or progressive AA show a much higher CLA-positivity compared to patients recovering from the disease and a decrease in percent CLA+ cells parallels a good clinical course. See Yano S., et al., *Acta Derm Venereol:* 82, 82 (2002). These studies therefore suggest that CLA+ lymphocytes may play an important role in AA. Xenograft models have demonstrated that activated T cells are likely to play a role in the pathogenesis of AA. Lesional scalp from AA patients grafted onto nude mice regrows hair coincident with a loss of infiltrating lymphocytes from the graft and, transfer of activated lesional T cells to SCID mice can transfer hair loss to human scalp explants on SCID mice. See Kalish R. S. & Gilhar A. *J Investig Dermatol Symp Proc:* 8, 164 (2003).

A variety of immunomodulating therapies are part of the usual treatment for this disorder however none of these treatments have been consistent in their efficacy. See Tang L., et al., *J Invest Dermatol:* 120, 400 (2003); Tang L., et al., (2004); and Tang L., et al., *J Am Acad Dermatol:* 49, 1013 (2003). Neutralizing anti-IL-31RA antibody or fragment thereof or IL-31RA soluble receptor (IL-31RA and IL-31RA/OSMRbeta soluble receptors) may be effective to limit, reduce, inhibit, or prevent the effects of the development of AA.

Acne Vulgaris/Acne Rosacea

Acne vulgaris, a disorder of the pilosebaceous apparatus, is the most common skin problem of adolescence. Abnormalities in follicular keratinization are thought to produce the acne lesion. Acne rosacea is differentiated from acne vulagaris by the presence of red papules, pustules, cysts and extensive telangiectasias, but the absence of comedones (white heads). Increased sebum excretion from sebaceous glands is a major factor in the pathophysiology of acne vulgaris. Other sebaceous gland functions are also associated with the development of acne, including sebaceous proinflammatory lipids; different cytokines produced locally; periglandular peptides and neuropeptides, such as corticotrophin-releasing hormone, which is produced by sebocytes; and substance P, which is expressed in the nerve endings at the vicinity of healthy-looking glands of acne patients. See Zouboulis C. C. *Clin Dermatol:* 22, 360 (2004).

Although the pathophysiology of acne vulgaris and acne rosacea remains unknown, clinical observations and histopathologic studies suggest that inflammation of the pilosebaceous follicle may be central to the pathogenesis of rosacea and acne vulgaris. Early studies on analysis of T cell subsets infiltrating rosacea legions indicated that the majority of T cells expressed CD4. See Rufli T. & Buchner S. A. *Dermatologica:* 169, 1 (1984).

CD4+ T cells produce IL-31 and IHC analysis of skin for IL-31 expression suggests that IL-31 is expressed in sebaceous and sweat glands. IL-31 stimulation of epidermal keratinocytes induces expression of chemokines which likely results in cellular infiltration suggesting that IL-31 may contribute to the pro-inflammatory response in skin. IL-31 may therefore contribute to the pathophysiology of acne rosacea and acne vulgaris. Accordingly, an IL-31RA antagonist, such as an anti-IL-31RA antibody or fragment thereof, or an IL-31RA soluble receptor (IL-31RA and IL-31RA/OSMRbeta soluble receptors) can be useful to treat, reduce the severity of, inhibit the progression of, ablate, and/or eliminate one or more symptoms associated with acne rosacea and acne vulgaris.

Prurigo Nodularis

Prurigo nodularis is an eruption of lichenified or excoriated nodules caused by intractable pruritus that is difficult to treat. While chronic rubbing results in lichenification, and scratching in linear excoriations, individuals who pick and gouge at their itchy, irritated skin tend to produce markedly thickened papules known as prurigo nodules. Although prurigo nodularis is not specific to atopic dermatitis, many patients with these nodules also have an atopic reaction, which manifests as allergic rhinitis, asthma, or food allergy. T cells represent the majority of infiltrating cells in prurigo lesions and these lesions often represents the most pruritic skin lesion in atopy patients.

Topical treatment of prurigo nodularis with capsaicin, an anti-pruritic alkaloid that interferes with the perception of pruritis and pain by depletion of neuropeptides like substance P in small sensory cutaneous nerves, has proven to be an effective and safe regimen resulting in clearing of the skin lesions. See Stander S., et al., *J Am Acad Dermatol:* 44, 471 (2001). Studies of the itch response in NC/Nga mice using capsaicin treatment showed that the spontaneous development of dermatitis lesions was almost completely prevented. Furthermore, the elevation of serum IgE levels was significantly suppressed and infiltrating eosinophils and mast cell numbers in lesional skin of capsaicin treated mice were reduced. See Mihara K., et al., *Br J Dermatol:* 151, 335 (2004). The observations from this group suggest that scratching behaviour might contribute to the development of dermatitis by enhancing various immunological responses, therefore implying that prevention of the itch sensation and/or itch-associated scratching behaviour might be an effective treatment for AD. See Mihara K., et al., *Br J Dermatol:* 151, 335 (2004).

Chronic delivery of IL-31 induces pruritis and alopecia in mice followed by the development of skin lesions resembling dermatitis suggesting that IL-31 induces itching. See Dillon S. R., et al., *Nat Immunol:* 5, 752 (2004). The involvement of IL-31 was tested in induction of the itch response by two methods (i) capsaicin treatment of IL-31-treated mice and (ii) IL-31 treatment of Tac1 knockout mice, which have significantly reduced nociceptive pain responses because of lack of expression of neuropeptides in Example 5. In addition, whether neutralization of IL-31 in IL-31 treated mice could prevent pruritis and alopecia was tested in Example 5.

Skin-Tropic Viruses and Viral Associated Pruritis

Herpes Simplex Virus (HSV)-specific CD8+ T cells in the peripheral blood and HSV-specific CD8+ T cells recovered from herpes lesions express high levels of CLA where as non-skin-tropic herpes virus-specific CD8+ T cells lack CLA expression. See Koelle D. M., et al., *J Clin Invest:* 110, 537 (2002). HSV-2 reactive CD4+ T lymphocytes also express CLA, but at levels lower than those previously observed for CD8+ T lymphocytes. See Gonzalez J. C., et al., *J Infect Dis:* 191, 243 (2005). Pruritis has also been associated with herpes viral infections (See Hung K. Y., et al., *Blood Purif* 16, 147 (1998), though other viral diseases, like HIV, have also been associated with pruritic skin lesions. Severe, intractable pruritus, often associated with erythematopapular skin lesions and hypereosinophilia, is a condition observed in some nonatopic, HIV-infected patients 36. See Singh F. & Rudikoff D, *Am J Clin Dermatol;* 4, 177 (2003); and Milazzo F., Piconi S., et al., *Allergy:* 54, 266 (1999).

The association of skin-tropic viruses with pruritis and CLA+ T cells suggests that IL-31 producing T cells may be involved in the pathophysiology of viral infections.

Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that antiinflammatory molecules, such as anti-IL-31RA antibodies and fragments thereof, and IL-31RA soluble receptors as described herein, could have crucial therapeutic potential for a vast number of human and animal diseases, from asthma and allergy to autoimmunity and septic shock. As such, use of anti-inflammatory anti-IL-31RA antibodies and fragments thereof, and IL-31RA soluble receptors as described herein can be used therapeutically as IL-31RA antagonists for treating, reducing the severity of, inhibiting the progression of, and ablating diseases such as arthritis, endotoxemia, inflammatory bowel disease, psoriasis, related disease and the like.

IL-31 has been shown to induce several chemokine and cytokine genes in normal human epidermal keratinocytes (NHEKs), including genes encoding GROα, (CXCL1), TARC (CC117), MIP3β, (CCL19), MDC (CCL22), MIP-3 (CCL23), MIP-1β (CCL4), and I-309. See Dillon S. R., et al., *Nat Immunol:* 5, 752 (2004). TARC and MDC bind CCR4, a chemokine receptor associated with Th2-type T cells and predominantly expressed by CLA+ T cells in peripheral blood. Both chemokines have been implicated in the recruitment of T cells into the skin of AD patients suggesting that these chemokines contribute to the inflammatory process associated with the pathogenesis of AD. See Example 10 for a model to measure the reduction in TARC and MDC levels by administering an IL-31 antagonist.

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk Although it is highly visible, psoriasis is not a contagious disease. The pathogenesis of the diseases involves chronic inflammation of the affected tissues. Anti-IL-31RA antibodies and fragment thereof and soluble receptors (IL-31RA and IL-31RA/OSMRbeta soluble receptors) could serve as a valuable therapeutic to treat, inhibit the progression of, reduce the severity of, reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

The present invention provides a method for inhibiting activation or differentiation of monocytes/macrophages. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation.

The molecules of the present invention have particular use in the monocyte/macrophage arm of the immune system. Methods are known that can assess such activity. For example, interferon gamma (IFN-γ) is a potent activator of mononuclear phagocytes. For example, an increase in expression of IL-31RA upon activation of THP-1 cells (ATCC No. TIB-202) with interferon gamma could suggest that this receptor is involved in monocyte activation. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation. Moreover, monocyte-macrophage function has been shown to be abnormal in a variety of diseased states. For example see, Johnston, R B, *New Eng. J. Med.* 318:747-752, 1998.

One of skill in the art would recognize that agonists of IL-31RA receptor, such as agonist IL-31RA antibody, are useful. For example, depressed migration of monocytes has been reported in populations with a predisposition to infection, such as newborn infants, patients receiving corticosteroid or other immunosuppressive therapy, and patients with diabetes mellitus, burns, or AIDS. Agonists for IL-31RA, such as agonist IL-31RA antibody, could result in an increase in the ability of monocytes to migrate and possibly prevent infection in these populations. There is also a profound defect of phagocytic killing by mononuclear phagocytes from patients with chronic granulomatous disease. This results in the formation of subcutaneous abscesses, as well as abscesses in the liver, lungs, spleen, and lymph nodes. An agonist of IL-31RA receptor such as agonist IL-31RA antibody, could correct or improve this phagocytic defect. In addition, defective monocyte cytotoxicity has been reported in patients with cancer and Wiskott-Aldrich syndrome (eczema, thrombocytopenia, and recurrent infections). Activation of monocytes by agonists of IL-31RA receptor, such as agonist IL-31RA antibody, could aid in treatment of these conditions. The monocyte-macrophage system is prominently involved in several lipid-storage diseases (sphingolipidoses) such as Gaucher's disease. Resistance to infection can be impaired because of a defect in macrophage function, which could be treated by agonists to IL-31RA receptor such as agonist IL-31RA antibody.

Using methods known in the art, and disclosed herein, one of skill could readily assess the activity of IL-31RA agonists and antagonists in diseases that have a high correlation of CLA+ T cells. In addition, as IL-31 is expressed in a T-cell, macrophage and monocyte-specific manner, and these diseases involve abnormalities in monocytic cells, such as cell proliferation, function, localization, and activation, the polynucleotides, polypeptides, and antibodies of the present invention can be used to as diagnostics to detect such monocytic cell abnormalities, and indicate the presence of disease. Such methods involve taking a biological sample from a patient, such as blood, saliva, or biopsy, and comparing it to a normal control sample. Histological, cytological, flow cytometric, biochemical and other methods can be used to determine the relative levels or localization of IL-31, or cells expressing IL-31, i.e., monocytes, in the patient sample compared to the normal control. A change in the level (increase or decrease) of IL-31 expression, or a change in number or localization of monocytes (e.g., increase or infiltration of monocytic cells in tissues where they are not normally present) compared to a control would be indicative of disease. Such diagnostic methods can also include measuring TARC and MDC, for example. Such methods are well known in the art and disclosed herein.

IL-31RA antagonists, such as anti-IL-31RA antibodies, can be used to modulate the immune system by binding IL-31RA receptor, and thus, preventing the binding of IL-31 with endogenous IL-31 receptor. Alternatively, IL-31RA antagonists, such as soluble IL-31RA and IL-31RA/OSMR-beta receptors, can also be used to modulate the immune system by inhibiting the binding of IL-31 with the endogenous IL-31RA receptor. Accordingly, the present invention includes the use of IL-31RA antibodies and fragments thereof as well as IL-31RA soluble receptors (IL-31RAa do IL-31RA/OSMRbeta) which can be administered to a subject which has excess IL-31. IL-31RA antagonists (e.g., anti-IL-31RA antibodies and fragments thereof and soluble IL-31RA and soluble IL-31RA/OSMRbeta receptors) can be also used to treat diseases that have a high correlation of CLA+ T cells. Suitable subjects include mammals, such as humans.

IL-31 has been shown to be expressed in activated mononuclear cells, and may be involved in regulating inflammation. As such, antibodies and soluble receptors of the present invention can be assayed and used for their ability to modify inflammation, or can be used as a marker for inflammation. Methods to determine proinflammatory and anti-inflammatory qualities of IL-31 are known in the art and discussed herein. Moreover, it may be involved in up-regulating the production of acute phase reactants, such as serum amyloid A (SAA), α1-antichymotrypsin, and haptoglobin, and that expression of IL-31RA receptor may be increased upon injection of lipopolysaccharide (LPS) in vivo that are involved in inflammatory response (Dumoutier, L. et al., *Proc. Nat'l. Acad. Sci.* 97:10144-10149, 2000). Production of acute phase proteins, such as SAA, is considered a short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, J. *Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, where a ligand such as IL-31 that acts as a pro-inflammatory molecule and induces production of SAA, antagonists would be useful in treating inflammatory disease and other diseases associated with acute phase response proteins induced by the ligand. Such antagonists are provided by the present invention. For example, a method of reducing inflammation comprises administering to a mammal with inflammation a therapeutically effective amount of a composition comprising anti-IL-31RA antibody (e.g., neutralizing antibody) or fragment thereof, or a soluble receptor (e.g., IL-31RA and IL-31RA/OSMRbeta soluble receptors) that is sufficient to reduce inflammation. Moreover, a method of suppressing an inflammatory response in a mammal with inflammation can comprise: (1) determining a level of serum amyloid A protein; (2) administering a composition comprising an anti-IL-31RA antibody as described herein or soluble receptor (IL-31RA and IL-31RA/OSMRbeta soluble receptors) in an acceptable pharmaceutical carrier; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Moreover, anti-IL-31RA antibodies and fragments thereof that block the binding and/or signaling of IL-31 to IL-31RA, and soluble IL-31RA receptors (IL-31RA and IL-31RA/OSMRbeta) that bind IL-31 and thus prevent the binding of IL-31 to cellular-based IL-31RA are useful to antagonize or block signaling of IL-31 and are thus useful in the treatment of, inhibit the progression of, reduce the severity of, reduce one or more symptoms associated with Contact dermatitis, Drug induced delayed type cutaneous allergic reactions, Toxic epidermal necrolysis, Cutaneous T cell Lymphoma, Bullous pemphigoid, Alopecia aereata, Vitiligo, Acne Rosacea, Prurigo nodularis, Scleroderma, and Herpes simplex virus.

Anti-IL-31RA antibodies, and soluble IL-31RA (IL-31RA and IL-31RA/OSMRbeta soluble receptors) comprising receptors are useful as antagonists of IL-31. Such antagonistic effects can be achieved by direct neutralization or binding of its natural ligand. In addition to antagonistic uses, the soluble receptors can bind IL-31 and act as carrier or carrier proteins, in order to transport IL-31 to different tissues, organs, and cells within the body. As such, the soluble receptors can be fused or coupled to molecules, polypeptides or chemical moieties that direct the soluble-receptor-Ligand complex to a specific site, such as a tissue, specific immune cell, monocytes, or tumor. For example, in acute infection or some cancers, benefit may result from induction of inflammation and local acute phase response proteins. Thus, the soluble receptors described herein or antibodies (and fragments thereof) of the present invention can be used to specifically direct the action of a pro-inflammatory IL-31 ligand. See, Cosman, D. *Cytokine* 5: 95-106, 1993; and Fernandez-Botran, R. *Exp. Opin. Invest. Drugs* 9:497-513, 2000.

IL-31 may also be used within diagnostic systems for the detection of circulating levels of ligand, and in the detection of acute phase inflammatory response. Within a related embodiment, antibodies or other agents that specifically bind to IL-31, e.g., soluble IL-31RA and soluble IL-31RA/OSMRbeta, can be used to detect circulating IL-31 polypeptides. Elevated or depressed levels of ligand or receptor polypeptides may be indicative of pathological conditions, including inflammation or cancer. Moreover, detection of acute phase proteins or molecules such as IL-31 can be indicative of a chronic inflammatory condition in certain disease states (e.g., rheumatoid arthritis). Detection of such conditions serves to aid in disease diagnosis as well as help a physician in choosing proper therapy.

Generally, the dosage of administered IL-31RA antibody or fragment thereof or soluble IL-31RA receptor or soluble IL-31RA/OSMRbeta receptor will vary depending upon such factors as the patient's age, weight, height, sex, general medical condition and previous medical history. Typically, it is desirable to provide the recipient with a dosage of IL-31RA antibody or fragment thereof or soluble IL-31RA receptor or soluble IL-31RA/OSMRbeta receptor which is in the range of from about 1 pg/kg to 10 mg/kg (amount of agent/body weight of patient), although a lower or higher dosage also may be administered as circumstances dictate. One skilled in the art can readily determine such dosages, and adjustments thereto, using methods known in the art.

Administration of IL-31RA antibody or fragment thereof or soluble IL-31RA receptor or soluble IL-31RA/OSMRbeta receptor to a subject can be topical, intradermal, inhalant, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-31RA antibody or fragment thereof or soluble IL-31RA receptor or soluble IL-31RA/OSMRbeta receptor can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of transcutaneous administration (Mitragotri et al., *Science* 269:850 (1995)). Transdermal delivery using electroporation provides another means to administer IL-31RA antibody or fragment thereof or soluble IL-31RA receptor or soluble IL-31RA/OSMRbeta receptor (Potts et al., *Pharm. Biotechnol.* 10:213 (1997)).

A pharmaceutical composition comprising a IL-31RA antibody or fragment thereof (antagonist and agonist) or a soluble IL-31RA receptor or a soluble IL-31RA/OSMRbeta receptor can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, an IL-31RA antibody or fragment thereof (antagonist and agonist) or a soluble IL-31RA receptor or a soluble IL-31RA/OSMRbeta receptor and a pharmaceutically acceptable carrier are administered to a patient in a therapeutically effective amount. A combination of an IL-31RA antibody (antagonist and agonist) or a soluble IL-31RA receptor (e.g., IL-31RA homodimer and a zcytor17/OSMRbeta heterodimer) and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates at least a portion of the inflammatory response.

A pharmaceutical composition comprising an IL-31RA antibody or fragment thereof (antagonist and agonist) or a soluble IL-31RA receptor or a soluble IL-31RA/OSMRbeta receptor can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

An IL-31RA antibody or fragment thereof (antagonist and agonist) or a soluble IL-31RA receptor or a soluble IL-31RA/OSMRbeta receptor can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

EXAMPLES

Example 1

Determination of Human Primary T Cell Types that Express IL-31 Upon Stimulation

Selection of Study Subjects and Biopsies

Twelve patients with AD (moderate to severe disease; median age was 32 years old with skin involvement of 5-45%), 6 patients with psoriasis (median age was 56 years old with skin involvement of 10-65%) and 12 healthy individuals (median age 34 years) were included in A study after informed consent. None of the patients had received any systemic corticosteroids previously. All patients were off topical corticosteroids for one week before their skin biopsy or blood drawing. Two mm punch biopsies were taken from 1) acute erythematous AD lesions of less than three days' onset, 2) chronic, lichenified AD lesions of greater than two weeks' duration, 3) chronic psoriasis lesions, and 4) normal skin. The skin samples were immediately frozen at −70° C. for immunohistochemistry or Western and immuno-dot blotting.

Isolation and Activation of Primary Human T Cell Subsets:

To isolate various T cell subsets, human PBMCs from the donors were isolated using standard Ficoll gradient centrifugation. Total T cells were then isolated using the T Cell Isolation Kit II (Miltenyi Biotec) according to the manufacturer's instructions. Separation efficiency was assessed using standard flow cytometry and determined to be >95% T cells. To separate CD45RA+ "naïve" T cells from the CD45RO+ "memory" T cells, the total T cell population was incubated with anti-CD45RO microbeads (Miltenyi Biotec) for 15 minutes at +4° C. and magnetically separated according to the manufacturers instructions. The naïve and memory T cell populations were determined to be >90% pure by flow cytometry.

CD45RO+ memory T cells are often tissue specific and cutaneous lymphocyte antigen (CLA) is used to differentiate skin-homing T cells from gut-homing T cells expressing α4/β7 on their surface. To determine which of these cell types produce IL-31, CLA+ T cells were isolated from total T cells, activated and conditioned media was collected for the IL-31 bioassay. To do this, total T cells were isolated and then incubated on ice for 20 minutes in 1 mL of a 1:50 dilution of anti-CLA-FITC antibody (PharMingen). Cells were then washed, resuspended in MACS buffer and incubated with anti-FITC microbeads (Miltenyi Biotec) for 15 minutes at +4° C. The cells were then washed, resuspended and magnetically separated over an LS column according to the manufacturer's instructions. The labeled T cells were later determined to be >80% pure while the CLA-depleted T cells were >98% CLA−. Both CLA+ and CLA− T cells were collected and cultured concurrently.

To activate the CD45RA+ and CD45RO+ T cell subsets, cells were cultured overnight in 24-well tissue culture plates pretreated with 2.0 µg/mL anti-CD3 antibody (Southern Biotechnology). The cells were plated at a concentration of $2.5 \times 10^6$ cells/mL in tissue culture media (RPMI, 5% fetal bovine serum, L-Glutamine and Sodium Pyruvate (all Gibco)) supplemented with 2.0 µg/mL anti-CD28 (Southern Biotechnology) and placed in a +37° C. incubator. After four hours, half of the wells were harvested, cells pelleted and conditioned media frozen at −20° C. until time of IL-31 bioassay.

The CLA+ and CLA− T cell subsets were activated similarly in 48-well tissue culture plates that were pretreated with 2.0 µg/mL anti-CD3 antibody (Southern Biotechnology). The cells were activated for 16 hours or 24 hours in a +37° C. incubator at a concentration of $6.25 \times 10^5$ cells/mL. Samples were harvested, cells pelleted and conditioned media frozen at −20° C. until time of IL-31 bioassay. For suboptimal activation, CLA+ T cells were cultured in plates pre-treated with 0.5 ug/ml of anti-CD3 antibody.

Human IL-31 Bioassay Protocol:

BAF3 cells transfected with hIL-31RA, hOSMRbeta, and KZ134 were grown to $5 \times 10^5$ and $1 \times 10^6$ cells/mL. Cells were washed with assay media (RPMI 1640, 10% FBS, L-Glutamine, Sodium Pyruvate, and Pen/Strep (all Gibco)) and resuspended at $3 \times 10^5$ cell/mL in assay medium. In a 96-well opaque plate, hIL-31 standards were titered in duplicate from 600 pg/mL to 9.38 pg/mL in assay medium via a 100 µL/well, 1:2 serial dilution. Quality control standards were added in duplicate to the plate at 350 pg/mL and 35 pg/mL in 100 µL. Test samples were often diluted 1:2 or 1:4 and added in duplicate to the sample wells. 100 µL of the washed BAF3 cells were then added to each well for a final concentration of $3 \times 10^4$ cells/well. The plate was then incubated for 16-24 hours at +37° C. in a 5% $CO_2$ incubator. The plate was then centrifuged at 1200 RPM for 5 minutes, media flicked off and 25 µL/well of lysis buffer (Promega) added to each well. After 10 minutes the plate was read on a luminometer (Berthold). The luminometer added 40 µL/well of luciferase substrate mix (Promega) and integrated the luminescence for a period of 4 seconds. Luminescence values were exported to a spreadsheet where they were analyzed and converted into picograms of IL-31 per $10^6$ cells per mL of volume. The data is summarized in Table 1.

Results of IL-31 Bioassay:

The results from the CD45RA+ and the CD45RO+ T cell samples revealed that IL-31 was primarily produced by activated CD45RO+ memory T cells. The CD45RA+ and CD45RO+ T cells from both donors produced no detectable IL-31 when unstimulated. However, the CD45RO+ samples from both donors #3 and #4 generated significant levels of IL-31 following a 24 hour activation with plate-bound anti-CD3 and soluble anti-CD28 (110.4 pg/$10^6$ cells/mL and 145.6 pg/$10^6$ cells/mL respectively). Conversely, when the CD45RA+ T cells from donors #3 and #4 were activated with anti-CD3 and anti-CD28, they produced very low amounts of IL-31 (13.1 pg/$10^6$ cells/mL and 12.7 pg/$10^6$ cells/mL respectively).

The CLA+ and CLA− T cell samples revealed that IL-31 seems to be made almost entirely by activated CLA+ T cells. The CLA− population of T cells (which includes naïve T cells, a4/β7 gut-homing memory T cells, and tissue uncommitted T cells) from both donors generated no detectable levels of IL-31 regardless of time point or activation condition. The CLA+ T cells on the other hand, generated very high levels of IL-31 when stimulated with 2.0 µg/mL plate-bound anti-CD3 antibody. Donor #5 generated 1385.7 pg/$10^6$ cells/mL IL-31 by 16 hours and >1920 pg/$10^6$ cells/mL by 24 hours. Donor #6 generated 121.3 pg/$10^6$ cells/mL IL-31 at 16 hours and 328.9 pg/$10^6$ cells/mL IL-31 at 24 hours. These results clearly demonstrate that of the T cell subsets, IL-31 seems to be made specifically by cutaneous (CLA+) T cells under standard activation conditions.

TABLE 1

| Donor# | Cell Type | Activation | IL-31 (pg/$10^6$ cells/mL) 6 hr | IL-31 (pg/$10^6$ cells/mL) 24 hr |
|---|---|---|---|---|
| 3 | CD45RA+ | αCD3 + αCD28 | Below Detection | 13.1 |
| 3 | CD45RO+ | αCD3 + αCD28 | 8.6 | 110.4 |
| 4 | CD45RA+ | αCD3 + αCD28 | 6.7 | 12.7 |
| 4 | CD45RO+ | αCD3 + αCD28 | 11.9 | 145.6 |
| | | | 16 hr | 24 hr |
| 5 | CLA+ T Cells | Unstimulated | Below Detection | Below Detection |
| 5 | CLA+ T Cells | αCD3 | 1385.7 | >1920 |
| 5 | CLA− T Cells | Unstimulated | Below Detection | Below Detection |
| 5 | CLA− T Cells | αCD3 | Below Detection | Below Detection |
| 6 | CLA+ T Cells | Unstimulated | Below Detection | Below Detection |
| 6 | CLA+ T Cells | αCD3 | 121.3 | 328.9 |
| 6 | CLA− T Cells | Unstimulated | Below Detection | Below Detection |
| 6 | CLA− T Cells | αCD3 | Below Detection | Below Detection |

Example 2

IL-31 Involvement in Initiation and Perpetuation of Contact Hyper-Sensitivity

Method I

BALB/c mice are painted on shaved mid-back with 25 µl of 0.5% DNFB dissolved (2,4, dinitro-fluoro-benzene, Sigma, St. Louis, Mo.) in acetone:olive oil (4:1) solution using a pipettor. A vehicle control group receives 25 µl of acetone:olive oil only. After 5 days, mice are anaesthetized with isofluorane in an inhalation chamber and both ear pinnae of experimental and control animals are measured with an engineer's micrometer (Mitutoyo) to obtain a baseline measurement. Mice are then challenged by applying 10

µl of 0.25% DNFB in acetone:olive oil (4:1) to both sides of each ear of all mice. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice.

Whole blood and serum for FACS and/or ELISA analysis are collected prior to sacrifice and ears are collected for histology.

Method II (Induces Th2 Responses)

BALB/c mice are painted on shaved mid-back with 100 ul of 0.5% FITC (fluorescein isothiocyanate) in a 1:1 solution of acetone/dibutyl phthalate (MSDS available using pipettor on days 1, 2 and 8. On day 13, mice are anaesthetized with isofluorane in an inhalation chamber and both ear pinnae of experimental and control animals are measured with an engineer's micrometer (Mitutoyo) to obtain a baseline measurement. Mice are challenged by applying 25 ul of 0.5% FITC (in 1:1 acetone/dibutyl phthalate) to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Method III (Induces Th1 Responses)

BALB/c mice are painted on shaved mid-back with 25 ul of 2% oxazalone (in 4: lacetone/olive oil) using pipettor. On day 7, mice are anaesthetized with isofluorane in an inhalation chamber and both ear pinnae of experimental and control animals are measured with an engineer's micrometer (Mitutoyo) to obtain a baseline measurement. Mice are challenged by applying 8 ul of oxazalone to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Involvement of IL-31 in the initiation and perpetuation of contact hyper-sensitivity is tested using a neutralizing antibody against IL-31 both at the sensitization and challenge phases of the experiment.

Example 3

IL-31 Involvement in Atopic Dermatitis
Methods I (Sensitization of NC/Nga Mice)

Male NC/Nga mice were purchased from Charles River Laboratories, Japan. The mice were 4 weeks old on arrival and housed in SPF quarantine conditions for 4 weeks to acclimate. The mice were approximately 10-11 weeks old at the start of the antigen sensitization. Mice were anaesthetized with isofluorane and backs were shaved with electric clippers. Approximately 10 ug of *Dermatophagoides pteronyssinus* (Dp) (Indoor Biotechnologies, Charlottesville, Va., special order) extract was injected intradermally at the nape of the neck 3 times per week for 5 to 6 weeks until mice developed skin lesions. Control animals received 10 ul PBS intradermal injections 3 times per week. The Dp extract was prepared according to method by Matsuoka and colleagues. Matsuoka H., et al., *Allergy:* 58, 139 (2003). Briefly, 595 mg Dp lyophilized spent culture extract was dissolved in 12 mL sterile PBS (Gibco). Dp was mixed in a 50 mL Falcon tube on a shaking rocker for 30 minutes. The extract was spun for 10 minutes at 2000 rpm and the supernatant was collected and aliquoted into 1 mL cryovial tubes and stored at −20° C.

Method II (Sensitization of DO11.10 Mice)

DO11.10 transgenic mice were bred from an in-house colony and were between 9.5 and 14 weeks old at start of antigen sensitization. Twenty-four hours prior to epicutaneous sensitization mice were anaesthetized with isofluorane and the entire trunk (back and abdomen) of mice were shaved with electric clippers. The mice were then tape stripped with Elastin surgical tape (Johnson and Johnson) on the back. One $cm^2$ sterile gauze patches were wetted with either 500 ug ovalbumin (Calbiochem 32467) or sterile PBS (Gibco) and adhered to left backside of mice with DuoDerm Extra Thin Dressing (ConvaTec 187932). The patch and dressing were then covered in a body wrap of the Elastin surgical tape so mice could not remove or destroy the patches. Patches were worn for 7 days and removed. The mice were rested for two weeks before having another round of epicutaneous sensitization. Mice received a total of three one-week sensitizations.

Results

Immunohistochemical analysis of IL-31RA expression in lesional and non-lesional skin from dust mite sensitized NC/Nga and OVA sensitized DO11.10 animals showed that IL-31RA is expressed by epidermal keratinocytes in mice, however no significant difference in levels of expression can be found between antigen sensitized versus PBS sensitized animals Example 4

IL-31 Involvement Delayed Type Hypersensitivity
Methods

To generate a DTH response, mice were sensitized to antigen on day 0 by subcutaneous immunization at the base of the tail with 100 ug ovalbumin (OVA) in complete Freund's adjuvant (CFA, 50-100 µl total volume). One week later mice were anesthetized with isofluorane in an inhalation chamber and both ear pinnae of experimental and control animals were measured with an engineer's micrometer (Mitutoyo) to obtain a baseline measurement. Mice were challenged intradermally with 10 ug OVA in PBS in a total volume of 10 µl into the left ear pinnae, just below the skin without hitting any veins. As a control, mice also received an injection of 10 µl PBS in the right ear pinnae. In some cases, a separate control group given an i.d. injection of OVA in the ear may also be treated with topical corticosteroids as a positive control to inhibit the reaction. At 24 and 48 hr after challenge, mice were anesthetized and ear thickness was measured. Results were expressed as: Specific ear swelling=(24 hr measurement−0 hr measurement) for experimental ear−(24 hr measurement−0 hr measurement) for negative control ear. Induration, the hallmark of DTH, is detectable by 18 hours after injection of sensitized antigen and is maximal by 24-48 hours. The lag in the onset of palpable induration is the reason for naming the response "delayed type."

Results

IL-31 transgenic mice were tested for DTH, however, due to an increase in ear thickness in un-challenged IL-31 transgenic animals, no statistically significant difference in DTH could be determined between IL-31 Tg animals compared to wildtype controls. IL-31RA knockout animals were also tested in a DTH response and no significant difference in the DTH response could be observed between receptor knockout and wildtype animals.

Example 5

IL-31 Involvement in Induction of the Itch Response

Methods I (IL-31 Treatment of Capsaicin Pre-Treated Mice)

Ten week old BALB/c animals (CRL) were anaesthetized and injected with a long-lasting analgesic agent, bupranorphine hydrochloride, subcutaneously at 0.1 mg/kg before injection of 0.25 ml of 4 mg/ml solution of capsaicin in 10% ethanol+10% Tween-80 in saline subcutaneously into scruff of neck. Animals were kept anaesthetized for at least 30 min following neurotoxin treatment. Forty-eight hours later, 14-day osmotic pumps were implanted subcutaneously for continuous delivery of 20 ug/day of IL-31 for 14 days. Mice were monitored daily for 6 days for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results demonstrated that while non-capsaicin-treated mice showed a mean scratch/hairloss score of 2.625 following three days of IL-31 delivery, capsaicin-treated mice showed a significantly lower score of 1. Thus mice treated with capsaicin prior to IL-31 delivery showed both a delay in incidence of scratching and hairloss and a lower score in the intensity of scratching and hairloss over the six days of the experiment. These data suggest that IL-31 does induce some neuronal component that contributes to the alopecia and pruritis induced by IL-31. Therefore, neutralization of IL-31 may decrease the incidence and intensity of itch, and therefore dermatitis, in patients suffering from skin disorders that involve itch.

Method II (IL-31 Treatment of Tac1 Gene Deficient Mice)

Mice that are homozygous null for the Tac1 gene express no detectible substance P or neurokinin A These mice have significantly reduced nociceptive pain responses to moderate to intense stimuli and are therefore a useful tool for studying the contribution of tachykinin peptides to pain/itch processing and inflammatory disease states. Twelve week old, Tac1 knockout mice were implanted with 14-day osmotic pumps delivering 1 µg/day of IL-31 protein and observed daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results of this study show that Tac1 deficient mice were less susceptible to IL-31 induced scratching/hairloss compared to wildtype control mice. While 100% (10/10) of wildtype mice had developed evidence of scratching and hairloss by day 6 of IL-31 treatment, only 33.3% (2/6) Tac1 deficient mice were showing signs of scratching and hairloss at the same time-point. These data show that IL-31 induces a neuronal component that contributes to the scratch/hairloss phenotype in IL-31-treated mice and neutralization of IL-31 may decrease the incidence and intensity of scratching in the context of dermatitis.

Method III (Effect of Administration of IL-31 Neutralizing Antibody on IL-31 Treated Mice)

Normal female BALB/c mice (CRL) approximately 8 to 12 weeks old were implanted subcutaneously with 14-day osmotic pumps (Alzet, #2002) delivering 1 µg/day mIL-31. Groups of mice received intraperitoneal (i.p.) injections of rat anti-mouse IL-31 monoclonal antibody 10 mg/kg (200 ug/mouse) twice weekly starting 1 week prior to IL-31 delivery. Control groups of mice received i.p. injections of vehicle (PBS/0.1% BSA) with the identical dosing schedules. Mice were scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

In all experiments, mice treated with rat anti-mIL-31 mAb had a delay in onset of symptoms of approximately 5 to 7 days and a lower overall score for alopecia and pruritis. All groups of mAb treated mice (regardless of dose frequency or concentration) developed alopecia and pruritis similar to control mice by 13 day of the study. These data suggest that neutralization of IL-31 can delay the onset of the scratch/hairloss response induced by IL-31.

Example 6

Immunohistochemical (IHC) Staining of IL-31 in Skin Lesions from Uninvolved Psoriatic, and Atopic Dermatitis Uninvolved psoriatic, atopic dermatitis and normal skin were tested for the IL-31 ligand by IHC. Positive control cells consisted of BHK cells transfected with IL-31. Negative controls performed included: (1) un-transfected BHK cells, (2) staining representative tissues and cells with protein A purified Normal Rabbit serum and detecting antibody binding as usual. Antibody reagent was E5758 (Rabbit anti-huIL-31 CEE, Aff. Purified at 1.0 mg/ml). Control cells included C02-6020: BHK cells expressing zcytor17 Lig hu-CEE/21, and a BHK wild type. Tissues tested included acute atopic dermatitis skin samples, chronic atopic dermatitis skin samples, unaffected area skin samples, and normal control skin samples and other in-house control samples.

The cells and tissues described above were fixed overnight in 10% NBF and embedded in paraffin using standard techniques.

Five µM sections were baked at 61° C. for 30 min for tissue adhesion. Slides were subsequently dewaxed in 3×5' in xylene and rehydrated through graded alcohols as follows: 2×2' in 100% EtOH, 2×2' in X95% EtOH, 1×2' in 70% EtOH. Slides were rinsed in dH20, and then heat induced epitope retrieval (HIER) was performed for 20 minutes under steam followed by 20 minutes cooling to RT in 10 mM Tris, 1 mM EDTA, pH 9.0

Slides were loaded onto a DakoCytomation Autostainer. Slides were rinsed with TBS/Tween buffer (TBST), prepared as recommend by manufacturer. Endogenous biotin was blocked with a 10 minute incubation in avidin solution, washed in TBST followed by a 10 minute incubation in biotin solution. Slides were washed in TBST. A protein block (PBSB) (0.5% Blocking Powder in PBS, Perkin Elmer NEL700001KT.) was applied for 30 minutes and rinsed off slides. The primary antibody was diluted to 500 ng/ml and was applied for 60 minutes in ChemMate Antibody Dilution Buffer (part # ADB250, Ventana Medical systems).

Tissues washed twice in TBST, and then incubated 45 minutes in biotinylated Goat anti-Rabbit Ab, 750 ng/ml in PBSB (catalog # BA-1000, Vector Labs). Slides washed twice in TBST. Vectastain Elite ABC Reagent (catalog # PK-7100, Vector Labs) was incubated for 45 minutes. Slides washed twice in TBST. Signals were developed with DAB+ (catalog # K-3468, DakoCytomation) for 10 minutes at room temperature. Tissue slides were then counterstained in hematoxylin (catalog # H-3401 Vector Labs), dehydrated and coverslipped in VectorMount (catalog # H-5000, Vector Labs).

Results

Cell Controls:

BHK cells transfected with IL-31 was positively stained with IL-31 antibody E5758 while un-transfected cells was negative for this antibody. The same transfected and un-transfected cells were negative with anti-rabbit sera.

2) Atopic Dermatitis Skin Analysis:

The staining pattern for IL31 in the AD skin samples is identical to that of psoriasis skins reported previously: keratinocyte and CD3 positive T-cells stained negative for IL31. A weak but rather uniform staining of the epithelial cells in the secretory portion of the sweat glands was present, but a strong signal was observed in the inner layer of epithelium in the duct portion. Sebaceous gland was positive for IL31. There was no difference in the IL31 staining between AD and normal skin.

Immunohistochemical (IHC) staining of uninvolved psoriatic, atopic dermatitis and normal skin showed strong staining of IL-31 in the holocrine secretion of the sebaceous glands. Considering the phenotype of IL 31 transgenic mice, it is interesting to note that the sebaceous glands originate as an epithelial bud from the outer root sheath of hair follicles. In addition to sebaceous glands weak but rather uniform staining of IL-31 was observed in the epithelial cells in the secretory portion of the sweat glands and a strong signal in the inner layer of epithelium was observed in the duct portion of sweat glands.

Example 7

Immunohistochemical (IHC) Staining of IL-31RA in Uninvolved Psoriatic, and Atopic Dermatitis Uninvolved psoriatic, atopic dermatitis and normal skin were tested for the IL-31RA by IHC. Positive control cells consisted of BHK cells dual transfected with IL-31RA and OSMR. Negative controls performed included: (1) un-transfected BHK cells, (2) staining representative tissues and cells with protein A purified Normal Rabbit serum and detecting antibody binding as usual. Antibody reagent was E6292 (Rabbit anti-huIL-31RAs-CEE v0.4 at 1.33 mg/ml). Control cells included C02-5117 BHK cells expressing human IL-31RA and human OSMR (Total cells in the pellet: $3.9 \times 10^6$, vitality was >90%) and C04-1587: BHK wild type (Total cells in the pellet: $5 \times 10^6$). Other tissues examined included: 5 Acute atopic dermatitis skin samples, 10 Chronic atopic dermatitis skin samples, 10 Unaffected area skin samples, Normal control skin samples, and other in-house skin samples.

The cells and tissues described above were fixed overnight in 10% NBF and embedded in paraffin using standard techniques.

Five μM sections were baked at 61° C. for 30 min for tissue adhesion. Slides were subsequently dewaxed in 3×5' in xylene and rehydrated through graded alcohols as follows: 2×2' in 100% EtOH, 2×2' in X95% EtOH, 1×2' in 70% EtOH. Slides were rinsed in dH20, and then heat induced epitope retrieval (HIER) was performed for 20 minutes under steam followed by 20 minutes cooling to RT in 10 mM Tris, 1 mM EDTA, pH 9.0

Slides were loaded onto a DakoCytomation Autostainer. Slides were rinsed with TBS/Tween buffer (TBST), prepared as recommend by manufacturer. Endogenous biotin was blocked with a 10-minute incubation in avidin solution, washed in TBST followed by a 10-minute incubation in biotin solution. Slides were washed in TBST. A protein block (PBSB) (0.5% Blocking Powder in PBS, Perkin Elmer NEL700001KT.) was applied for 30 minutes and rinsed off slides. Primary antibodies diluted from 665 ng/ml to 1330 ng/ml for IL31RA were applied for 60 minutes in Chem-Mate Antibody Dilution Buffer (part # ADB250, Ventana Medical systems).

Tissues were washed twice in TBST, and then incubated 45 minutes in biotinylated Goat anti-Rabbit Ab, 750 ng/ml in PBSB (catalog # BA-1000, Vector Labs). Slides were washed twice in TBST. Vectastain Elite ABC Reagent (catalog # PK-7100, Vector Labs) was incubated for 45 minutes. Slides were washed twice in TBST. Signals were developed with DAB+ (catalog # K-3468, DakoCytomation) for 10 minutes at room temperature. Tissue slides were then counterstained in hematoxylin (catalog # H-3401 Vector Labs), dehydrated and coverslipped in VectorMount (catalog # H-5000, Vector Labs).

Results are shown in Table 2.

TABLE 2

Results of IHC for IL-3 IRA in Skin Biopsies from Acute and Uninvolved AD Compared to Normal Volunteers

| CASE ID | IL-31RA IHC SCORE* | CD3 IHC SCORE* |
| --- | --- | --- |
| AD-1 | 2-3 | 0-1 |
| AD-2 | 2-3 | 2 |
| AD-3 | 2-3 | 1-2 |
| AD-4 | 3 | 1 |
| AD-5 | 2 | 2 |
| UAD-1 | 1-2 | 1 |
| UAD-2 | 1 | 0-1 |
| UAD-3 | ND | ND |
| UAD-4 | ND | ND |
| UAD-5 | 1-2 | 0-1 |
| UAD-6 | 2-3 | ND |
| UAD-7 | 2 | 1 |
| UAD-8 | 1 | 1 |
| UAD-9 | 1-2 | 1 |
| UAD-10 | 2 | ND |
| Normal-1 | 1 | 0-1 |
| Normal-2 | 0-1 | 0-1 |
| Normal-3 | 1 | 0-1 |

Abbreviations:
AD: atopic dermatitis;
UAD: uninvolved AD;
ND: Not Done
*IHC signal was scored from 0 (no signal) to 4 (intense signal)

There was a slight up regulation of IL31RA in the epidermis of AD skin samples. Possibly a small percentage of CD3 positive T-cells were positive for IL31RA in the AD skins. There were CLA positive cells in all skin samples tested. AD skins may have more CLA positive cells than that of the normal or UAD samples.

IL-31RA was also expressed in the epithelial cells of eccrine sweat glands with the cuboidal epithelial cells in the secretory portion of the eccrine glands demonstrating slightly higher level of IL-31RA protein compared to the duct portion.

Collectively, these data demonstrate that IL-31RA is expressed by epidermal keratinocytes from both control volunteers and AD patients. However, the levels of IL-31RA expressed on keratinocytes from AD skin biopsies were higher than the levels observed in skin biopsies from normal controls, indicating a potential for increased responsiveness to IL-31 in the context of AD.

IL-31RA was also found expressed on a subset of perivascular infiltrating cells present in skin biopsies from AD patients but was not present in control skin biopsies. These IL-31RA+ cells were recognized by an antibody specific for the tissue macrophage marker CD68, indicating these cells were skin-infiltrating tissue macrophages.

Example 8

Isolation of Skin Infiltrating cells by Laser Capture Microscopy and Analysis of IL-31MRNA by RT-PCR The presence of skin infiltrating T cells is a distinguishing feature in skin biopsies from AD patients compared to normal individuals. Since IL-31 is a T cell associated cytokine, the expression of IL-31 in skin-infiltrating T cells in tissue biopsies from AD patients was examined. First, the presence of increased numbers of CD3+ T cells in skin tissue biopsies from AD patients compared to normal individuals was confirmed by IHC. See Table 2. Next, laser capture microscopy was used to specifically isolate skin infiltrating cells for analysis of IL-31 mRNA by RT-PCR. IL-31 mRNA was expressed by skin infiltrating cells from acute AD patients. In normal tissues, infiltrating cells are not normally found and therefore could not be tested. However, the epidermal keratinocyte layer, which is present in both AD and normal skin, was analyzed for IL-31 mRNA expression and lower levels of IL-31 mRNA were found in normal samples compared to the epidermal keratinocyte layer of AD samples. Semi-quantitative analysis of IL-31 mRNA expression compared to an internal control gene (HPRT) showed that although IL-31 mRNA levels were not significantly different between AD and normal samples, there was a trend towards higher IL-31 expression in skin from AD patients.

Example 9

IL-31 is Produced by Memory T Cells with a Skin-Homing Phenotype

Analysis of skin biopsies confirmed that the infiltrating CD3+ T cells in the skin, which express IL-31 mRNA, express the skin-homing marker cutaneous lymphocyte antigen (CLA). Of the total T cell population in normal human peripheral blood, IL-31 expression was found to be largely restricted to CD45RO+ memory/effector cells as opposed to the CD45RA+ naïve T cell population.

In order to determine if IL-31 production was associated with CLA+ skin-homing T cells, CLA+ and CLA− T cells were isolated from peripheral blood of patients diagnosed with AD and control volunteers and compared IL-31 mRNA and protein levels following anti-CD3 plus anti-CD28 stimulation. Our results indicate that IL-31 mRNA was significantly elevated in CLA+ T cells from both AD and normal individuals at both 4 h (p0.0087 and p0.0022 CLA+ compared to CLA− for AD and normal, respectively) and 24 h (p0.0022 CLA+ compared to CLA− for both AD and normal samples) post stimulation. Analysis of IL-31 protein levels in culture supernatants confirmed that IL-31 was produced predominantly by CLA+ T cells as there was no detectible IL-31 in culture supernatants from CLA− T cells from both AD and control individuals. There were no significant differences in IL-31 levels between AD and normal patients. We also analysed the production of IL-31 by peripheral blood T cells that express other tissue-specific homing markers, such as the gut-specific homing marker α4β7, from normal volunteers. Comparison of the IL-31 levels produced by CLA+ T cells and α4β7+ cells demonstrated CLA+ T cells preferentially produce IL-31 compared to the α4β7+ cells (average of 34.5 pg/ml and 14.42 pg/ml IL-31, respectively).

Although both AD patients and normal controls have circulating CLA+ T cells that express IL-31 upon activation, CLA+ T cells from AD patients are reported to exist in a more activated state compared to cells from normal individuals. Consequently, the threshold of stimulation required for the production of IL-31 by CLA+ T cells may differ between dermatitis patients and control subjects. To test this hypothesis, we stimulated CLA+ T cells from AD patients and control individuals with sub-optimal concentrations of anti-CD3 in the absence of anti-CD28 and analyzed the production of IL-31 in culture supernatants at 24 h after stimulation. Our results demonstrate that circulating CLA+ T cells from some AD patients produce higher levels of IL-31 compared to cells from normal individuals in this study with maximum levels reaching 1200 pg/mL, whereas maximal detected levels in normal CLA+ supernatants was only 400 pg/ml and maximal detected levels for psoriasis patients was 73 pg/ml at suboptimal concentrations of anti-CD3 stimulation. Five of eleven AD patients showed IL-31 levels below the limit of detection of our assay suggesting there might be a subset of AD patients where IL-31 is produced at low levels. This may reflect variations in the stage of disease of our study population. Nevertheless, more than half of the AD patients showed a trend towards higher IL-31 levels compared to psoriasis patients and normal individuals following suboptimal stimulation with anti-CD3. Since more CLA+ T cells are localized in skin of AD patients as compared to normal individuals, our studies suggest that there is an increased potential for IL-31 activity in the AD skin micro-environment. Thus, this study may suggest a subpopulation of AD patients, which have more activated CLA+ T cells producing IL-31.

Example 10

Reduction of TARC and MDC in Response to Anti-Il-31 Antibody in AD Mouse Models

Method I

Six-week old male NC/Nga mice (CRL Japan) were sensitized intradermally with 50 μg dust mite extract (*D. pteronyssinus*, Indoor Biotechnologies) three times a week on the back and scored for AD-like lesions. After 5 weeks of sensitization the mice were euthanized and the right ears were excised and placed into a single well of a 48-well culture dish (Corning) supplemented with RPMI+2% FBS (GIBCO Invitrogen). Plates were placed in 5% CO2 humidity controlled incubators. Supernatants were collected after 24 hours and frozen at −20° C. until further analysis.

Method II

Twelve-week old female NC/Nga mice (CRL Japan) were sensitized intradermally with 10 μg SEB (Toxin Technology) in the ear and on the back three times per week. The mice were scored for AD-like lesions. After 5 weeks of sensitization the mice were euthanized and 6 mm biopsy punches were taken from the injected ear of each mouse and placed into a single well of a 48-well culture dish supplemented with RPMI+2% FBS. Plates were placed in 5% CO2 humidity controlled incubators. Supernatants were collected after 24 hours and frozen at −20° C. until further analysis.

Groups of mice in both studies were treated with either a rat anti-mouse IL-31 monoclonal antibody at 10 mg/kg or vehicle, intraperitoneally two times each week starting after 1 to 2 weeks of sensitization.

TARC and MDC concentrations in the 24-hour supernatant samples were measured by conventional ELISA (R&D Systems).

TARC and MDC concentrations were lower in ear supernatants from anti-IL-31 treated mice compared to control mice in both studies, however, these results were not statistically significant when analyzed by ANOVA, probably due to small sample size. When the data from both experiments is combined and analyzed there is a statistically significant difference between treated groups.

---

What is claimed is:

1. A method of treating a patient with a skin disorder comprising administering a therapeutically effective amount of a pharmaceutical composition comprising an anti-Interleukin-31RA (IL-31RA) antibody and a pharmaceutically acceptable carrier to the patient, wherein the anti-IL-31RA antibody binds amino acid residues 20-519 of SEQ ID NO:6; and wherein the skin disorder is bullous pemphigoid.

2. The method of claim 1, wherein the anti-IL-31RA antibody is neutralizing.

3. The method of claim 1, wherein the Fc region of the anti-IL-31RA antibody is IgG, IgA, IgD, IgM or IgE.

4. The method of claim 1, wherein the Fc region of the anti-IL-31RA antibody is IgG.

5. The method of claim 1, wherein the anti-IL-31RA antibody is humanized.

* * * * *